US008519212B2

(12) United States Patent
Dairoku et al.

(10) Patent No.: US 8,519,212 B2
(45) Date of Patent: Aug. 27, 2013

(54) WATER-ABSORBENT RESIN, HYDROPOLYMER, PROCESS FOR PRODUCING THEM, AND USES OF THEM

(75) Inventors: Yorimichi Dairoku, Himeji (JP); Yoshio Irie, Himeji (JP); Shinichi Fujino, Himeji (JP); Yasuhiro Fujita, Himeji (JP); Takashi Azumi, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 423 days.

(21) Appl. No.: 12/777,373

(22) Filed: May 11, 2010

(65) Prior Publication Data

US 2010/0222758 A1 Sep. 2, 2010

Related U.S. Application Data

(62) Division of application No. 11/452,223, filed on Jun. 14, 2006, now Pat. No. 7,741,400, which is a division of application No. 10/942,851, filed on Sep. 17, 2004, now Pat. No. 7,091,253, which is a division of application No. 09/917,642, filed on Jul. 31, 2001, now Pat. No. 6,906,159.

(30) Foreign Application Priority Data

Aug. 3, 2000 (JP) ................................. 2000-235995
Nov. 15, 2000 (JP) ................................. 2000-348632

(51) Int. Cl.
*A61F 13/49* (2006.01)
*C08F 8/00* (2006.01)
*C08F 20/06* (2006.01)
*C08F 2/48* (2006.01)

(52) U.S. Cl.
USPC ............. 604/372; 522/33; 522/182; 524/832; 525/329.7; 525/385; 526/317.1; 526/930

(58) Field of Classification Search
USPC ................... 525/329.7, 385; 526/930, 317.1; 524/832; 604/372; 522/33, 182
See application file for complete search history.

(56) References Cited

U.S. PATENT DOCUMENTS

| 4,155,888 | A | 5/1979 | Mooth ............................ 527/314 |
|---|---|---|---|
| 4,525,527 | A | 6/1985 | Takeda et al. .................... 524/831 |
| 4,552,938 | A | 11/1985 | Mikita et al. .................... 526/240 |
| 4,703,067 | A | 10/1987 | Mikita et al. .................... 521/63 |
| 4,777,231 | A | 10/1988 | Bailey et al. .................... 526/203 |
| 4,820,742 | A | 4/1989 | Alexander et al. ............. 521/131 |
| 4,914,170 | A | 4/1990 | Chang et al. .................... 526/240 |
| 4,957,984 | A | 9/1990 | Itoh et al. ........................ 526/240 |
| 4,985,514 | A * | 1/1991 | Kimura et al. .................. 526/88 |
| 4,985,518 | A | 1/1991 | Alexander et al. ............. 526/240 |
| 5,258,448 | A | 11/1993 | Mallo et al. .................... 524/556 |
| 5,380,808 | A | 1/1995 | Sumiya et al. .............. 526/317.1 |
| 5,478,879 | A | 12/1995 | Kajikawa et al. .............. 524/500 |
| 5,883,158 | A | 3/1999 | Nambu et al. .................. 523/412 |
| 6,071,976 | A | 6/2000 | Dairoku et al. .................. 521/50 |
| 6,174,978 | B1 | 1/2001 | Hatsuda et al. ................. 526/240 |
| 6,187,828 | B1 | 2/2001 | Woodrum et al. .............. 521/64 |
| 6,228,930 | B1 | 5/2001 | Dairoku et al. ................. 524/500 |
| 6,313,231 | B1 | 11/2001 | Hosokawa et al. ............ 525/340 |
| 6,417,425 | B1 | 7/2002 | Whitmore et al. ............. 604/367 |
| 6,562,879 | B1 | 5/2003 | Hatsuda et al. .................. 521/56 |
| 2001/0025093 | A1 | 9/2001 | Ishizaki et al. ................. 526/210 |
| 2001/0053807 | A1 | 12/2001 | Miyake et al. ................. 524/239 |
| 2001/0053826 | A1 * | 12/2001 | Hosokawa et al. ............ 525/370 |

FOREIGN PATENT DOCUMENTS

| CN | 1224024 | 7/1999 |
|---|---|---|
| EP | 0206808 | 12/1986 |
| EP | 0207714 | 1/1987 |
| JP | 58208 | 4/1980 |
| JP | 147512 | 11/1980 |
| JP | 147809 | 11/1981 |
| JP | 71907 | 4/1983 |
| JP | 18712 | 1/1984 |
| JP | 275607 | 11/1988 |
| JP | 275608 | 11/1988 |
| JP | 165610 | 6/1989 |
| JP | 318022 | 12/1989 |
| JP | 129207 | 5/1990 |
| JP | 215801 | 8/1990 |
| JP | 175319 | 6/1992 |
| JP | 725935 | 1/1995 |
| JP | 7155591 | 6/1995 |
| JP | 9-67404 | 3/1997 |
| JP | 9124879 | 5/1997 |
| JP | 45812 | 2/1998 |
| JP | 182750 | 7/1998 |
| JP | 181005 | 7/1999 |
| JP | 228604 | 8/1999 |

OTHER PUBLICATIONS

Chen et al., An efficient preparation method for superabsorbent polymers, Journal of Applied Polymer Science, vol. 74, pp. 119-124 (1999).
Chemical Engineering Handbook, sixth edition, edited by Society of Chemical Engineers, published by Maruzan Co., Ltd. 1999, p. 843, Table 16.4.

* cited by examiner

*Primary Examiner* — Fred M Teskin
(74) *Attorney, Agent, or Firm* — Roylance, Abrams, Berdo & Goodman, L.L.P.

(57) ABSTRACT

The present invention provides a production process by which a water-absorbent resin of excellent quality can be obtained at a low cost by reasonable steps in aqueous solution polymerization. The process for producing a water-absorbent resin comprises the step of polymerizing an aqueous solution of water-absorbent resin-forming monomers including acrylic acid and/or its sodium salt as major components, wherein: (1) the aqueous solution has a monomer component concentration of not less than 45 weight %; (2) the polymerization is carried out while water is evaporated so that the ratio (concentration ratio) between a solid component concentration in a hydropolymer as formed by the polymerization and a solid component concentration in the aqueous monomer solution will not be less than 1.10; and (3) the solid component concentration in the hydropolymer as formed by the polymerization is not more than 80 weight %.

6 Claims, 8 Drawing Sheets

WATER-ABSORBENT RESIN, HYDROPOLYMER, PROCESS FOR PRODUCING THEM, AND USES OF THEM

This application is a divisional application of Ser. No. 11/452,223, filed Jun. 14, 2006, now U.S. Pat. No. 7,741,400, which is a divisional application of Ser. No. 10/942,851, filed Sep. 17, 2004, now U.S. Pat. No. 7,091,253, which is a divisional application Ser. No. 09/917,642, filed Jul. 31, 2001, now U.S. Pat. No. 6,906,159.

BACKGROUND OF THE INVENTION

A. Technical Field

The present invention relates to: a process for producing a water-absorbent resin which is utilized favorably for various uses such as sanitary articles (e.g. disposable diapers, sanitary napkins) and water-retaining agents for soil, wherein the water-absorbent resin is produced by polymerizing an aqueous solution of water-absorbent resin-forming monomers; products (hydropolymer and water-absorbent resin) from this process; and sanitary articles comprising the water-absorbent resin.

B. Background Art

In recent years, water-absorbent resins are widely utilized for various uses such as sanitary articles (e.g. disposable diapers, sanitary napkins, adult incontinent products) and water-retaining agents for soil and are produced and consumed in large quantities.

Particularly in the uses for the sanitary articles (e.g. disposable diapers, sanitary napkins, adult incontinent products), the tendency is toward increasing the amounts of water-absorbent resins and decreasing the amounts of pulp fibers in order to render products thin, and the water-absorbent resins are desired to have large absorption capacities under loads, while the water-absorbent resins are used in so large quantities per sheet of the sanitary articles that the water-absorbent resins are desired to cost low. Therefore, in the production line of the water-absorbent resins, it is desired to reduce energy consumption and waste matter emission and to thereby establish a reasonable production process.

Various polymerization processes have been attempted so far in which, for example, when aqueous solution polymerization of water-absorbent resin-forming monomers is carried out, a dried water-absorbent resin is obtained at one stroke by carrying out polymerization in a high monomer concentration or initiating polymerization at a high temperature to thereby vaporize water by a heat of polymerization or heating, for the purpose of rendering costs so low as to enhance the performance/cost ratio of the water-absorbent resin.

JP-A-071907/1983 (Arakawa Kagaku) and JP-A-018712/1984 (Arakawa Kagaku) disclose processes in which dry solids of water-absorbent resins are obtained at one stroke by polymerizing an aqueous acrylate salt solution of a concentration higher than 55 weight %. U.S. Pat. No. 4,985,518 (American Colloid) discloses a process in which a dry solid of a water-absorbent resin is obtained at one stroke by polymerizing an aqueous acrylate salt solution of a concentration higher than 30 weight %. JP-A-058208/1980 (Kitani) discloses a process in which polymerization is carried out in the polymerization temperature range of 106 to 160° C. without any crosslinking agent, and in examples thereof a dry solid having a low water content is formed at the end of the polymerization. JP-A-318022/1989 (Mitsubishi Yuka) discloses a process in which a polymer is obtained in almost a dry state by polymerizing an aqueous solution containing a monomer in a concentration of 45 to 80 weight % wherein the monomer has a neutralization ratio of 20 to 50 mol %. However, these processes have demerits in that the resultant water-absorbent resins have high extractable contents for their absorption capacities.

In addition, JP-A-147512/1980 (Sumitomo Chemical Co., Ltd.), JP-A-147809/1981 (Sumitomo Chemical Co., Ltd.), JP-A-275607/1988 (Sanyo Kasei), and JP-A-275608/1988 (Sanyo Kasei) disclose processes in which dried products of water-absorbent resins are obtained at one stroke by supplying aqueous monomer solutions onto heated rotary drums and then scraping off the resultant polymers therefrom. JP-A-165610/1989 (Rohm and Haas) also discloses almost the same process as the above in which a substantially dry solid of a water-absorbent resin is obtained by supplying an aqueous monomer solution onto a heated face. However, these processes also have the demerits in that the resultant water-absorbent resins have high extractable contents for their absorption capacities.

In addition, JP-A-215801/1990 (Mitsubishi Yuka) discloses a process in which polymerization is carried out by spraying into a gas phase an aqueous monomer solution as heated by utilizing a heat of neutralization of the monomer, but, as to this process, it is considered that the polymerization is difficult to control, because the polymerization is completed in about 3 seconds.

The above prior arts were published in or before 1990, but have their respective demerits, therefore it seems that they are not actually carried out.

Thereafter published were arts as directed to enhancement of the performance for the purpose of increasing the performance/cost ratio of the water-absorbent resin. JP-A-175319/1992 (Sanyo Kasei) and JP-A-181005/1999 (Nippon Shokubai Co., Ltd.) disclose attempts to obtain high-performance water-absorbent resins by initiating polymerization at a low temperature and mildly carrying out the polymerization while removing the generated heat to depress the peak temperature to not higher than about 90° C. JP-A-228604/1999 (Nippon Shokubai Co., Ltd.) discloses an attempt to obtain a high-performance water-absorbent resin still by initiating polymerization at a low temperature and mildly carrying out the polymerization while removing the generated heat to depress the peak temperature to not higher than about 95° C. or to control the increase of the solid component concentration within the range of 0.2 to 10 weight %. JP-A-067404/1997 (BASF) and U.S. Pat. No. 6,187,828 (BASF) disclose a process in which polymerization is initiated at a low temperature in a cylindrical polymerization reactor and carried out adiabatically, but this process has demerits in that the concentration of the aqueous monomer solution cannot be rendered high, because the heat removal is not carried out, and in that the residence time is long (several hours). All these processes sacrifice the productivity, therefore none of them can avoid high costs.

In addition, recently, "An Efficient Preparation Method for Superabsorbent Polymers" (Chen, Zhao) was reported in the Journal of Applied Polymer Science, Vol. 74, pp. 119-124 (1999). This proposes a low-cost polymerization process comprising the steps of placing an aqueous solution of a monomer concentration of 43.6% and an initiator into a stainless Petri dish, and then immersing this dish into a water bath of 70° C. or 80° C. to carry out polymerization. However, this process has not yet attained an industrially useful level.

In addition, JP-A-045812/1998 (Sekisui Chemical Products) discloses an attempt to inhibit bumping, promote emission of water vapor, and render the water content of the resultant gel low by adding short fibers to an aqueous monomer solution, but this attempt has the demerit of using expensive short fibers which do not contribute to the water absorption.

SUMMARY OF THE INVENTION

A. Object of the Invention

An object of the present invention is to provide a process by which a water-absorbent resin with excellent performance is produced at a low cost and, specifically, to provide by reasonable steps the following materials: a base polymer exhibiting a high absorption capacity without load and having a low extractable content; and a surface-crosslinked water-absorbent resin exhibiting a high absorption capacity under a load.

B. Disclosure of the Invention

The present inventors diligently studied to achieve the above object and, as a result, have completed the present invention by finding out that, on the contrary to the conventionally accepted theory (which is that, as is disclosed in the above JP-A-175319/1992 (Sanyo Kasei), JP-A-181005/1999 (Nippon Shokubai Co., Ltd.), and JP-A-228604/1999 (Nippon Shokubai Co., Ltd.), a high-performance water-absorbent resin is obtained by initiating the polymerization at a low temperature and by rendering the peak temperature as low as possible by the heat removal), a high-performance water-absorbent resin can be obtained with high productivity by a process in which a hydropolymer having a high solid component concentration is obtained in a short time by setting the polymerization initiation temperature for a high one and vaporizing water at the boiling point of the resulting gel and which therefore appears reckless in conventional views.

Herein, the term "hydropolymer" means a water-containing water-absorbent resin of which the solid component concentration is not more than 82 weight %.

In addition, important for the production process according to the present invention is how a hydropolymer having a high solid component concentration of 55 to 82 weight % which is formable by polymerization can be disintegrated. In the case where the hydropolymer, which is formed by polymerizing an aqueous solution of water-absorbent resin-forming monomers, has a shape difficult to dry as it is, such as shapes of thick plates, blocks, and sheets, the hydropolymer is usually disintegrated and then subjected to the steps such as drying, pulverization, classification, and surface crosslinking, thus forming a water-absorbent resin product. In cases of acrylic acid (salt)-based water-absorbent resins, a hydropolymer having a solid component concentration of less than 55 weight % can easily be disintegrated with such as meat-chopper-type disintegrating machines. In addition, like a dried hydropolymer, a hydropolymer having a solid component concentration of more than 82 weight % can easily be pulverized with such as conventional impact type pulverizing machines. However, a hydropolymer having a solid component concentration of 55 to 82 weight % is difficult to handle because of its properties and state, therefore an attempt to industrially disintegrate such a hydropolymer has not yet succeeded.

For example, in Comparative Examples 1 and 2 as set forth in U.S. Pat. No. 4,703,067 (American Colloid), hydropolymers having solid component concentrations of 58% and 67% respectively are obtained, but this USP teaches that "they cannot be pulverized as they are, so they needed to be dried before being pulverized". Thus, the disintegration in the above solid component concentration range is avoided in these Comparative Examples.

JP-A-175319/1992 (Sanyo Kasei) discloses a gel-disintegrating machine as an example, but the polymerization is carried out in a monomer concentration of 50 weight % at the highest, therefore this publication discloses no example of disintegration of a hydropolymer having a solid component concentration of not less than 55 weight %.

JP-A-119042/1998 (Nippon Shokubai Co., Ltd.), JP-A-188725/1999 (Nippon Shokubai Co., Ltd.), and JP-A-188726/1999 (Nippon Shokubai Co., Ltd.) disclose that a gel is disintegrated by shearing it with a fixed blade and a rotary blade, but still these publications disclose no example of disintegration of a hydropolymer having a solid component concentration of not less than 55 weight %.

JP-A-188727/1999 (Hatsuda, Miyake, Yano on Nippon Shokubai Co., Ltd.) discloses that a hydropolymer is disintegrated by shearing it by interposing it between a pair of spiral rotary blades which are arranged opposite to each other and fed at speeds different from each other. In Example 1 as set forth in this publication, a hydropolymer having a water content of 39 weight % is disintegrated, but this publication does not disclose any example in which the hydropolymer is disintegrated into particles of which the weight-average diameter is not larger than 100 mm. Actually, the weight-average particle diameter of the disintegrated hydropolymer was larger than 100 mm.

Thus, the present inventors diligently studied about how a hydropolymer having a high solid component concentration of 55 to 82 weight % which is formable by polymerization can be disintegrated. As a result, the present inventors have further found out that such a hydropolymer can easily be divided into fine pieces with a specific disintegrating machine.

That is to say, a process for producing a water-absorbent resin, according to the present invention, comprises the step of polymerizing an aqueous solution of water-absorbent resin-forming monomers including acrylic acid and/or its sodium salt as major components, wherein:

(1) the aqueous solution has a monomer component concentration of not less than 45 weight %;

(2) the polymerization is carried out while water is evaporated so that the ratio (concentration ratio) between a solid component concentration in a hydropolymer as formed by the polymerization and a solid component concentration in the aqueous monomer solution will not be less than 1.10; and (3) the solid component concentration in the hydropolymer as formed by the polymerization is not more than 80 weight %.

Another process for producing a water-absorbent resin, according to the present invention, comprises the step of polymerizing an aqueous solution of water-absorbent resin-forming monomers including acrylic acid and/or its salt as major components, wherein:

(1) the highest temperature during the polymerization is not lower than 100° C.;

(2) the polymerization initiation temperature is not lower than 50° C.; and (3) acrylic acid and/or water which evaporate during the polymerization are collected and recycled.

Another process for producing a water-absorbent resin, according to the present invention, comprises the step of polymerizing an aqueous solution of water-absorbent resin-forming monomers including acrylic acid and/or its salt as major components, wherein:

(1) the polymerization initiation temperature is not lower than 50° C.;

(2) the solid component concentration in a hydropolymer as formed by the polymerization is not more than 80 weight %; and (3) the polymerization time is shorter than 3 minutes.

Another process for producing a water-absorbent resin, according to the present invention, comprises the step of polymerizing an aqueous solution of water-absorbent resin-forming monomers including acrylic acid and/or its salt as major components, wherein:

(1) at least one photoinitiator and at least one thermal initiator are used together as polymerization initiators; and (2) the highest temperature during the polymerization is not lower than 105° C.

Another process for producing a water-absorbent resin, according to the present invention, comprises the step of polymerizing an aqueous solution of water-absorbent resin-forming monomers including acrylic acid and/or its salt as major components, wherein:

(1) at least one photoinitiator and at least one thermal initiator are used together as polymerization initiators;

(2) the polymerization initiation temperature is not lower than 50° C.; and (3) the aqueous solution has a monomer component concentration of not less than 45 weight %.

Another process for producing a water-absorbent resin, according to the present invention, comprises the step of polymerizing an aqueous solution of water-absorbent resin-forming monomers including acrylic acid and/or its sodium salt as major components, wherein:

(1) the neutralization ratio of acrylic acid is not less than 50 mol %;

(2) the polymerization initiation temperature is not lower than 50° C.;

(3) the solid component concentration in a hydropolymer as formed by the polymerization is not more than 80 weight %; and (4) the polymerization time is shorter than 3 minutes.

Another process for producing a water-absorbent resin, according to the present invention, comprises the step of polymerizing an aqueous solution of water-absorbent resin-forming monomers including acrylic acid and/or its salt as major components, wherein:

(1) the polymerization initiation temperature is not lower than 50° C.;

(2) the aqueous solution has a monomer component concentration of not less than 45 weight %; and (3) the polymerization temperature-rising ratio is not more than 0.30.

Another process for producing a water-absorbent resin, according to the present invention, comprises the step of polymerizing an aqueous solution of water-absorbent resin-forming monomers including acrylic acid and/or its sodium salt as major components, wherein:

(1) the polymerization initiation temperature is not lower than 50° C.;

(2) the aqueous solution has a monomer component concentration of not less than 45 weight %; and (3) the highest temperature during the polymerization is not higher than 140° C.

Another process for producing a water-absorbent resin, according to the present invention, comprises the step of polymerizing an aqueous solution of water-absorbent resin-forming monomers including acrylic acid and/or its sodium salt as major components, wherein:

(1) the aqueous solution has a monomer component concentration of not less than 45 weight %;

(2) the neutralization ratio of acrylic acid is not less than 50 mol %;

(3) the polymerization initiation temperature is not lower than 50° C.; and (4) the difference between the polymerization initiation temperature and the highest temperature during the polymerization is not more than 70° C.

Another process for producing a water-absorbent resin, according to the present invention, comprises the step of polymerizing an aqueous solution of water-absorbent resin-forming monomers including acrylic acid and/or its salt as major components, wherein the polymerization proceeds under extension force.

Another process for producing a water-absorbent resin, according to the present invention, comprises the step of polymerizing an aqueous solution of water-absorbent resin-forming monomers including acrylic acid and/or its salt as major components, wherein the process further comprises the step of disintegrating a hydropolymer into particles of which the weight-average diameter is not larger than 100 mm wherein the hydropolymer is formed by the polymerization and has a solid component concentration in the range of 55 to 82 weight %.

Another process for producing a water-absorbent resin, according to the present invention, comprises the step of polymerizing an aqueous solution of water-absorbent resin-forming monomers including acrylic acid and/or its salt as major components, wherein the process further comprises the step of disintegrating a hydropolymer with a disintegrating machine having a screen wherein the hydropolymer is formed by the polymerization and has a solid component concentration in the range of 55 to 82 weight %.

Another process for producing a water-absorbent resin, according to the present invention, comprises the step of polymerizing an aqueous solution of water-absorbent resin-forming monomers including acrylic acid and/or its salt as major components, wherein the process further comprises the step of disintegrating a hydropolymer with a disintegrating machine so that the ratio of the increase of the solid component concentration during the disintegration may not be less than 2 points wherein the hydropolymer is formed by the polymerization and has a solid component concentration in the range of 55 to 82 weight %.

Another process for producing a water-absorbent resin, according to the present invention, comprises the step of polymerizing an aqueous solution of water-absorbent resin-forming monomers including acrylic acid and/or its salt as major components, wherein the process further comprises the step of disintegrating a hydropolymer with a disintegrating machine while passing a gas through the disintegrating machine wherein the hydropolymer is formed by the polymerization and has a solid component concentration in the range of 55 to 82 weight %.

Another process for producing a water-absorbent resin, according to the present invention, comprises the step of polymerizing an aqueous solution of water-absorbent resin-forming monomers including acrylic acid and/or its salt as major components, wherein the process further comprises the step of surface-crosslinking a particulate hydropolymer which is obtained by disintegrating a hydropolymer resultant from the polymerization and has a solid component concentration in the range of 55 to 82 weight %, a residual monomer content of not more than 1,000 ppm, and a weight-average particle diameter of not larger than 3 mm.

Another process for producing a water-absorbent resin, according to the present invention, comprises the step of polymerizing an aqueous solution of water-absorbent resin-forming monomers including acrylic acid and/or its salt as major components, wherein:

(1) the polymerization step produces a hydropolymer having a solid component concentration in the range of 55 to 82 weight %;

and wherein the process further comprises the following steps:

(2) a disintegration step for disintegrating the hydropolymer, which has a solid component concentration in the range of 55 to 82 weight %, into particles of which the weight-average diameter is not larger than 10 mm; and (3) a drying step for increasing the solid component concentration in the disintegrated hydropolymer by not less than 3%.

A water-absorbent resin, according to the present invention, is obtained by a process including the step of polymerizing an aqueous solution of water-absorbent resin-forming monomers including acrylic acid and/or its salt as major components, and has the following properties:

(1) 20 (g/g)≦absorption capacity without load (GV)≦60 (g/g);

(2) absorption capacity under a load (AAP)≧20 (g/g); and (3) absorption capacity without load (GV)×solubilization residue ratio (%)≦1,200 ((g/g) %).

A hydropolymer, according to the present invention, is a disintegrated hydropolymer which is obtained when producing a water-absorbent resin by a process including the step of polymerizing an aqueous solution of water-absorbent resin-forming monomers including acrylic acid and/or its salt as major components, and has a solid component concentration in the range of 55 to 82 weight %, a residual monomer content of not more than 1,000 ppm, and a weight-average particle diameter of not larger than 3 mm.

A sanitary article, according to the present invention, comprises at least one member selected from the group consisting of the water-absorbent resins obtained by the above production processes according to the present invention and the above water-absorbent resin according to the present invention.

These and other objects and the advantages of the present invention will be more fully apparent from the following detailed disclosure.

DETAILED DESCRIPTION OF THE INVENTION

Figure 1:
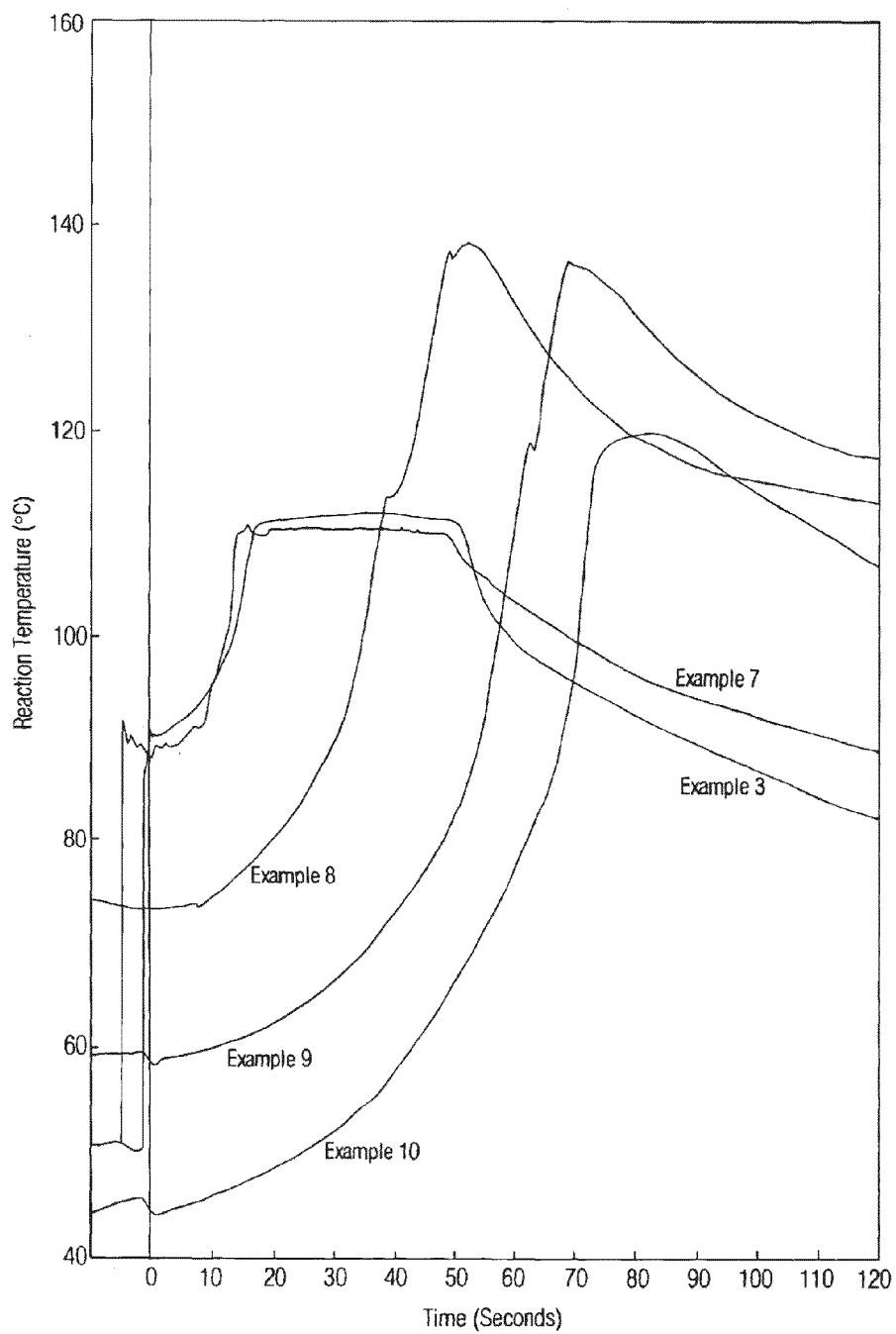
FIG. 1 is a graph which illustrates relations between polymerization reaction temperature and time in Examples 3 and 7 to 10, wherein the time zero is the initiation time of irradiation of light.

Hereinafter, modes for carrying out the present invention are explained in detail.

Examples of the water-absorbent resin-forming monomers, as used in the present invention, include anionic unsaturated monomers, such as (meth)acrylic acid, (anhydrous) maleic acid, itaconic acid, cinnamic acid, vinylsulfonic acid, allyltoluenesulfonic acid, vinyltoluenesulfonic acid, styrenesulfonic acid, 2-(meth)acrylamido-2-methylpropane sulfonic acid, 2-(meth)acryloylethanesulfonic acid, 2-(meth)acryloylpropanesulfonic acid, and 2-hydroxyethyl (meth)acryloyl phosphate, and their salts; mercaptan-group-containing unsaturated monomers; phenolic-hydroxyl-group-containing unsaturated monomers; amide-group-containing unsaturated monomers such as (meth)acrylamide, N-ethyl(meth)acrylamide, and N,N-dimethyl(meth)acrylamide; and amino-group-containing unsaturated monomers such as N,N-dimethylaminoethyl (meth)acrylate, N,N-dimethylaminopropyl (meth)acrylate, and N,N-dimethylaminopropyl(meth)acrylamide. These monomers may be used either alone respectively or fitly in combinations with each other. However, for performance and costs of the resulting water-absorbent resin, it is necessary to use acrylic acid and/or its salt (e.g. salts of such as sodium, lithium, potassium, ammonium, and amines, wherein the sodium salt is particularly favorable for costs) as major components. The acrylic acid and/or its salt is used in a ratio of favorably not less than 70 mol %, more favorably not less than 80 mol %, still more favorably not less than 90 mol %, particularly favorably not less than 95 mol %, to the entirety of the monomer components.

Besides the unsaturated monomer components such as acrylic acid and/or its salt and internal-crosslinking agents, other additives such as polymerization initiators as mentioned below are also included in the solid components in the aqueous monomer solution as referred to herein.

Conventional internal-crosslinking agents can be used as the above internal-crosslinking agents. Specific examples thereof include those which are disclosed on page 4 of JP-A-182750/1998. These internal-crosslinking agents may be used either alone respectively or in combinations with each other in consideration of their reactivity. Particularly, it is favorable that a compound with at least two polymerizable unsaturated groups is essentially used. The amount of the above internal-crosslinking agent, as used, is determinable fitly for the properties of the aimed water-absorbent resin.

The concentration of the water-absorbent resin-forming monomers is not especially limited, but is favorably not less than 30 weight %, more favorably not less than 35 weight %, still more favorably not less than 40 weight %, yet still more favorably not less than 45 weight %, yet still more favorably not less than 50 weight %, yet still more favorably not less than 55 weight %, yet still more favorably in the range of 30 to 70 weight %, yet still more favorably in the range of 35 to 60 weight %, yet still more favorably in the range of 40 to 60 weight %. In the case where the concentration is less than 30 weight %, the productivity is low. In the case where the concentration is more than 70 weight %, the absorption capacity is low.

The neutralization ratio of the acid-group-containing monomer is not especially limited, but is favorably not less than 50 mol %, more favorably in the range of 50 to 80 mol %

(but not including 80 mol %), still more favorably in the range of 55 to 78 mol %, most favorably in the range of 60 to 75 mol %, also considering that the neutralization subsequent to the polymerization is not needed for uses having a possibility of contact with human bodies, such as sanitary articles.

In the case where acrylic acid is used in the form neutralized with an alkali, it is favorable that a heat of neutralization and/or a heat of dissolution (of acrylic acid and an alkali) is effectively utilized for raising the temperature of the aqueous monomer solution. In a favorable mode for carrying out the present invention, the polymerization is initiated by adding a crosslinking agent and an initiator to the aqueous monomer solution as heated by the neutralization in an adiabatic state or, as is mentioned below, the heat of neutralization and/or the heat of dissolution (of acrylic acid and the alkali) are utilized for removal of dissolved oxygen.

When the polymerization is carried out, the following materials may be added to the reaction system: hydrophilic polymers such as starch, its derivatives, cellulose, its derivatives, poly(vinyl alcohol), poly(acrylic acid) (or its salts), and crosslinked polymers of poly(acrylic acid) (or its salts); chain transfer agents such as hypophosphorous acid (or its salts); and chelating agents.

With regard to the method for polymerizing the above monomer components, there is no especial limitation if it is aqueous solution polymerization. For example, the present invention can be carried out by static polymerization in which the aqueous monomer solution is polymerized in a static state or by agitation polymerization in which the aqueous monomer solution is polymerized in an agitation apparatus.

In the static polymerization method, an endless belt is favorably used. Favorable examples of the belt include resin-made or rubber-made belts such that the heat of polymerization is difficult to escape from the face (of the belts) contacting the materials.

In the agitation polymerization method, single-shaft agitators are also available, but multiple-shaft agitators are favorable.

In cases of the radical aqueous solution polymerization, conventionally, dissolved oxygen which hinders the polymerization is removed from the aqueous solution by blowing an inert gas into the aqueous solution or deaerating the aqueous solution under reduced pressure before the polymerization initiator is added. In the actual circumstances, however, facilities and operation costs are needed therefor. In a favorable mode for carrying out the present invention, the operation for removing the dissolved oxygen is carried out by utilizing the aforementioned heat of neutralization and/or the aforementioned heat of dissolution (of acrylic acid and the alkali) for raising the temperature of the aqueous monomer solution and thereby volatilizing the dissolved oxygen.

In a more favorable mode for carrying out the present invention, raw materials (such as acrylic acid, an aqueous alkali solution, and water) for the aqueous monomer solution can be heated by neutralization without being deoxidized beforehand, so that the dissolved oxygen content can be adjusted to favorably not more than 4 ppm, more favorably not more than 2 ppm, most favorably not more than 1 ppm, of the aqueous monomer solution, and then the aqueous monomer solution can be subjected to the polymerization intactly without deoxidation operation.

In addition, it is also favorable that a part or all of the raw materials (such as acrylic acid, an aqueous alkali solution, and water) for the aqueous monomer solution are beforehand partially deoxidized and then further deoxidized by raising the temperature by the neutralization and In addition, in the case where the polymerization is initiated at a high temperature of not lower than 80° C. by line-mixing acrylic acid and an alkali to make neutralization and further line-mixing a polymerization initiator, it is favorable for inhibition of the polymerization initiation in lines that the raw materials (such as acrylic acid, an aqueous alkali solution, and water) are not deoxidized beforehand.

The polymerization is carried out usually under normal pressure, but it is also a favorable mode that the polymerization is carried out while water is distilled off under reduced pressure in order to lower the boiling temperature of the polymerization system. More favorably for such as easiness of the operation, the polymerization is carried out under normal pressure.

The increase of the neutralization ratio during the polymerization is not especially limited, but is favorably not less than 2 points, more favorably not less than 3 points, still more favorably not less than 4 points. Even if the increase of the neutralization ratio is 0, there is no especial problem. However, the increase of the neutralization ratio of not less than 2 points has the advantage of enhancing the properties of the resultant polymers (hydropolymer, base polymer, water-absorbent resin).

The polymerization initiator, as used in the present invention, is not especially limited, but usable examples thereof include: thermal initiators (e.g. persulfates such as sodium persulfate, potassium persulfate, and ammonium persulfate; peroxides such as hydrogen peroxide, t-butyl peroxide, and methyl ethyl ketone peroxide; azo compounds such as azonitrile compounds, azoamidine compounds, cyclic azoamidine compounds, azoamide compounds, alkylazo compounds, 2,2'-azobis(2-amidinopropane) dihydrochloride, and 2,2'-azobis(2-(2-imidazolin-2-yl)propane) dihydrochloride); and photoinitiators (e.g. benzoin derivatives, benzyl derivatives, acetophenone derivatives, benzophenone derivatives, azo compounds). Considering the costs and the ability to reduce the residual monomer content, the persulfates are favorable. In addition, the use of the at least one photoinitiator and ultraviolet rays is also a favorable method. More favorably, the at least one thermal initiator and the at least one photoinitiator are used together.

It is favorable to beforehand render the monomer temperature high. The reason therefor is that such a way facilitates the aforementioned removal of dissolved oxygen and further makes it possible to immediately realize the below-mentioned favorable polymerization initiation temperature. Such a monomer temperature is not especially limited, but is usually not lower than 50° C., favorably not lower than 60° C., more favorably not lower than 70° C., still more favorably not lower than 80° C., yet still more favorably not lower than 90° C., yet still more favorably in the range of 80 to 105° C., most favorably in the range of 90 to 100° C. In the case where the monomer temperature is lower than 50° C., the induction period and the polymerization time lengthen so much as to deteriorate not only the productivity but also the properties of the resulting water-absorbent resin. Incidentally, the polymerization time is a period of time of from completion of the polymerization initiation conditions following the charge of the aqueous monomer solution into a polymerization reactor till attainment to the peak temperature.

The polymerization initiation temperature is usually not lower than 50° C., favorably not lower than 60° C., more favorably not lower than 70° C., still more favorably not lower than 80° C., yet still more favorably not lower than 90° C., yet still more favorably in the range of 80 to 105° C., most favorably in the range of 90 to 100° C. In the case where the polymerization initiation temperature is lower than 50° C., the induction period and the polymerization time lengthen so much as to deteriorate not only the productivity but also the properties of the resulting water-absorbent resin. In the case where the polymerization initiation temperature is higher than 105° C., the foaming or extension might not sufficiently occur. The polymerization initiation temperature can be observed from such as white turbidity, increase of viscosity, and rise of temperature of the aqueous monomer solution.

Incidentally, as is aforementioned, the heat of neutralization of the aqueous monomer solution and/or the heat of dissolution (of acrylic acid and the alkali) are favorably utilized for securing the temperature of this aqueous monomer solution to cause the polymerization initiation.

The highest temperature during the polymerization is not especially limited, but is favorably not higher than 150° C., more favorably not higher than 140° C., still more favorably not higher than 130° C., yet still more favorably not higher than 120° C., yet still more favorably not higher than 115° C. In the case where the highest temperature is higher than 150° C., there are disadvantages in that the properties of the resultant polymers (hydropolymer, base polymer, water-absorbent resin) are greatly deteriorated.

In the present invention, the difference between the polymerization initiation temperature and the highest temperature during the polymerization is favorably not more than 70° C., more favorably not more than 60° C., still more favorably not more than 50° C., yet still more favorably not more than 40° C., yet still more favorably not more than 30° C., most favorably not more than 25° C. In the case where the difference between the polymerization initiation temperature and the highest temperature during the polymerization is more than 70° C., there are disadvantages in that the properties of the resultant polymers (hydropolymer, base polymer, water-absorbent resin) are deteriorated.

The polymerization time is not especially limited, but is favorably not longer than 5 minutes, more favorably not longer than 3 minutes, still more favorably shorter than 3 minutes, yet still more favorably not longer than 2 minutes, yet still more favorably not longer than 1 minute. In the case where the polymerization time is longer than 5 minutes, there are disadvantages in that the productivity of the resultant polymers (hydropolymer, base polymer, water-absorbent resin) is deteriorated.

In a favorable example of the polymerization process according to the present invention, after the initiation of the polymerization, the temperature of the system rapidly rises to reach the boiling point in the stage of a low polymerization conversion, for example, of 10 to 20 mol %, at which the system emits water vapor and increases its solid component concentration, while the polymerization proceeds. Therefore, it is desirable that the heat radiation from portions (of the polymerization reactor) contacting the materials is suppressed as much as possible, and examples of qualities of materials as favorably used therefor include such that portions (made of such as resin, rubber, and stainless steel) non-contacting the materials are covered with heat insulators or heated with a jacket. The water vapor as emitted from the system might contain monomers. In such a case, therefore, the water vapor is desired to be recovered and recycled. Particularly, it is favorable that acrylic acid and/or water which evaporate during the polymerization are collected and recycled. The recovery ratio of the acrylic acid is favorably not less than 1%, more favorably not less than 2%, still more favorably not less than 3%, based on the whole weight (before neutralization) of the acrylic acid as used.

In addition, in the process according to the present invention, the polymerization is carried out at a high temperature from the initiation of the polymerization, and it is inferred that such polymerization is a cause of high performance. As to polymerization under normal pressure, a favorable mode thereof is a polymerization such that: when the polymerization conversion has reached 40 mol %, the temperature of the system has already been a temperature of not lower than 100° C., and even when the polymerization conversion has reached 50 mol %, the temperature of the system is still a temperature of not lower than 100° C. And a more favorable mode is a polymerization such that: when the polymerization conversion has reached 30 mol %, the temperature of the system has already been a temperature of not lower than 100° C., and even when the polymerization conversion has reached 50 mol %, the temperature of the system is still a temperature of not lower than 100° C. And the most favorable mode is a polymerization such that: when the polymerization conversion has reached 20 mol %, the temperature of the system has already been a temperature of not lower than 100° C., and even when the polymerization conversion has reached 50 mol %, the temperature of the system is still a temperature of not lower than 100° C. In cases of polymerization under reduced pressure, likewise, a favorable mode thereof is a polymerization such that: when the polymerization conversion has reached 40 mol %, the temperature of the system has already been the boiling temperature, and even when the polymerization conversion has reached 50 mol %, the temperature of the system is still the boiling temperature. And a more favorable mode is a polymerization such that: when the polymerization conversion has reached 30 mol %, the temperature of the system has already been the boiling temperature, and even when the polymerization conversion has reached 50 mol %, the temperature of the system is still the boiling temperature. And the most favorable mode is a polymerization such that: when the polymerization conversion has reached 20 mol %, the temperature of the system has already been the boiling temperature, and even when the polymerization conversion has reached 50 mol %, the temperature of the system is still the boiling temperature.

In this way, the system reaches a high temperature when the polymerization conversion is still low. Therefore, the time as needed for the polymerization is also short, and it is usual for the polymerization to end in not longer than 10 minutes, favorably not longer than 5 minutes. Incidentally, the time as needed for the polymerization is a period of time of from charge of a polymerization reactor with the aqueous monomer solution, to which the polymerization initiator has been added, till discharge of the resultant hydropolymer from the polymerization reactor.

In the present invention, it is desirable that the polymerization is carried out while water is evaporated so that the ratio (concentration ratio) between a solid component concentration in the hydropolymer as formed by the polymerization and a solid component concentration in the aqueous monomer solution will favorably not be less than 1.10, more favorably not be less than 1.15, still more favorably not be less than 1.20, yet still more favorably not be less than 1.25. In the case where the concentration ratio is less than 1.10, the utilization of the heat of polymerization cannot be said to be sufficient. Incidentally, the solid components in the aqueous monomer solution are monomers and other additives, and do not include water or solvents.

In the present invention, the ratio of temperature rising during the polymerization, namely, the ratio of $\Delta T$ (difference between the highest temperature during the polymerization and the polymerization initiation temperature; ° C.), as observed for the polymerization system, to theoretical $\Delta T$ (° C.), (the details of the calculation method for this ratio are described in the portion hereof under the heading of "DETAILED DESCRIPTION OF THE PREFERRED EMBODIMENTS") is favorably not more than 0.30, more favorably not more than 0.25, still more favorably not more than 0.20. In the case where the ratio of temperature rising during the polymerization is more than 0.30, the utilization of the heat of polymerization for the evaporation of water is so insufficient that there are disadvantages in that the properties of the resultant polymers (hydropolymer, base polymer, water-absorbent resin) are deteriorated.

The hydropolymer, as obtained by the above polymerization, has a solid component concentration of favorably not more than 82 weight %, more favorably not more than 80 weight %, still more favorably not more than 75 weight %. In addition, this solid component concentration is favorably in the range of 50 to 82 weight %, more favorably in the range of 55 to 82 weight %, still more favorably in the range of 60 to 78 weight %. yet still more favorably in the range of 60 to 75 weight %. yet still more favorably in the range of 60 to 73 weight %. yet still more favorably in the range of 66 to 73 weight %. In the case where this solid component concentration is more than 82 weight %, the deterioration of performance, namely, absorption capacity, and the increase of the extractable content are seen. In addition, in the case where this solid component concentration is less than 50 weight %, there are disadvantages in that a heavy burden is imposed on the subsequent drying step.

The above hydropolymer favorably has a form as produced by foaming expansion and shrinkage during the polymerization. As is illustrated by the photographs of FIGS. 3 to 7, this is a form which is made as a result that: the polymerization system foams into diameters on the cm to mm scale with a water vapor pressure due to boiling during the polymerization to become large in surface area, and further, to thereby promote the volatilization of water, and then the polymerization system shrinks. In addition, this form exhibits unexpected characteristics of having good releasability from the polymerization reactor and facilitating the disintegration of the hydropolymer.

The method for measuring the expansion magnification during the polymerization is described in the portion hereof under the heading of "DETAILED DESCRIPTION OF THE PREFERRED EMBODIMENTS". The expansion magnification during the polymerization is favorably not less than 2 times, more favorably not less than 3 times, still more favorably not less than 5 times, yet still more favorably not less than 10 times, yet still more favorably not less than 20 times. When expanding, the polymerization system is subjected to extension force, so the polymerization proceeds under extension force.

The above hydropolymer is divided into fine pieces, and then dried, and then pulverized, so that a base polymer (water-absorbent resin before being subjected to surface treatment) can be obtained.

From observation of the resultant base polymer with a microscope, it has been found that even if foaming occurs to the polymerization, most of particles are in a noncrystalline form which contains no bubble. The reason therefor seems to be that the bubble sizes during the foaming are relatively large.

In the production process according to the present invention, the base polymer may further be subjected to surface-crosslinking treatment, whereby a water-absorbent resin having a large absorption capacity under a load can be obtained. Usable for this surface-crosslinking treatment are conventional surface-crosslinking agents and conventional surface-crosslinking methods which are usually used for such a purpose.

Important for the production process according to the present invention is how a hydropolymer having a high solid component concentration of 55 to 82 weight % which is formable by polymerization can be disintegrated. In the case where the hydropolymer, which is formed by polymerizing an aqueous solution of water-absorbent resin-forming monomers, has a shape difficult to dry as it is, such as shapes of thick plates, blocks, and sheets, the hydropolymer is usually disintegrated and then subjected to the steps such as drying, pulverization, classification, and surface crosslinking, thus forming a water-absorbent resin product. In cases of acrylic acid (salt)-based water-absorbent resins, a hydropolymer having a solid component concentration of less than 55 weight % can easily be disintegrated with such as meat-chopper-type disintegrating machines. In addition, like a dried hydropolymer, a hydropolymer having a solid component concentration of more than 82 weight % can easily be pulverized with such as conventional impact type pulverizing machines. However, a hydropolymer having a solid component concentration of 55 to 82 weight % is difficult to handle because of its properties and state, therefore an attempt to industrially disintegrate such a hydropolymer has not yet succeeded.

Thus, the present inventors diligently studied about how a hydropolymer having a high solid component concentration of 55 to 82 weight % which is formable by polymerization can be disintegrated. As a result, the present inventors have found out that such a hydropolymer can easily be divided into fine pieces with a specific disintegrating or pulverizing machine (these are represented by the term "disintegrating machine" in the present patent application).

Incidentally, the shape of the hydropolymer having a solid component concentration of 55 to 82 weight % which is then subjected to the disintegration is not especially limited, but is favorably the shape of plates or sheets with a thickness of not larger than 3 cm, more favorably the shape of plates or sheets with a thickness of not larger than 2 cm, still more favorably the shape of plates or sheets with a thickness of not larger than 1 cm, yet still more favorably the shape of plates or sheets with a thickness of not larger than 5 cm in a much wrinkly form as formed by foaming expansion and shrinkage during the polymerization.

Disintegrating machines having a screen are favorable as apparatuses for disintegrating the hydropolymer having a solid component concentration of 55 to 82 weight % in the present invention. More favorable as such disintegrating machines are apparatuses corresponding to shearing type coarsely pulverizing machines or cutting and/or shearing mills which are classified into pulverizing machines as classified into pulverizing machines in Table 16.4 in the Chemical Engineering Handbook (6th revised edition, edited by the Chemical Engineering Society of Japan, published by Maruzen Co., Ltd. in 1999). Still more favorable are apparatuses to make disintegration by shearing between a fixed blade and a rotary blade. The disintegration with these apparatuses provides enablement for easily disintegrating the hydropolymer having a high solid component concentration of 55 to 82 weight % which has so far been difficult to disintegrate.

Specific examples of the shearing type coarsely pulverizing machines or cutting and/or shearing mills include the following:

SAWS, CIRCULAR SAWS, BAND SAW;
VERTICAL PULVERIZER (VERTICAL CUTTING MILL available from Orient Co., Ltd.);
ROTOPLEX available from Hosokawa Mikron Co., Ltd.;
TURBO CUTTER available from Turbo Kogyo Co., Ltd.;

TURBO GRINDER available from Turbo Kogyo Co., Ltd.;

TYRE SHREDDER available from Masuno Seisakusho Co., Ltd.;

ROTARY CUTTER MILL available from Yoshida Seisakusho Co., Ltd.;

CUTTER MILL available from Tokyo Atomizer Production Co., Ltd.;

SHRED CRUSHER available from Tokyo Atomizer Production Co., Ltd.;

CUTTER MILL available from Masuko Sangyo Co., Ltd.;

CRUSHER available from Masuko Sangyo Co., Ltd.;

ROTARY CUTTER MILL available from Nara Kikai Seisakusho Co., Ltd.;

GAINAX CRUSHER available from Horai Co., Ltd.;

U-COM available from Horai Co., Ltd.;

MESHMILL available from Horai Co., Ltd.;

In the present invention, it has been found out that when the hydropolymer having a solid component concentration in the range of 55 to 82 weight % is disintegrated with a disintegrating machine, if a contrivance is carried out in such a manner that the solid component concentration is increased by not less than 2 points (for example, the increase from 70 weight % to 72 weight % in the solid component concentration of the hydropolymer by the disintegration of the hydropolymer means an increase of 2 points in the solid component concentration) or that a gas, favorably dry air, is passed through the disintegrating machine or if both contrivances are carried out, then the hydropolymer is disintegrated even with a disintegrating machine of other than the cutting type wherein such disintegration of the hydropolymer is conventionally difficult.

As the ratio of the increase in the solid component concentration gets higher from 2 points to 3 points, 4 points or as the through-wind amount gets larger, the disintegration becomes easier. However, they should be selected considering economical aspects. When the disintegration is carried out, the water vapor as emitted from the hydropolymer might condense in the apparatus to easily cause the hydropolymer to adhere to the apparatus and to clog it up, but the through-wind is considered to prevent such phenomena from occurring.

In addition, the disintegration may involve addition of surfactants as disclosed in JP-A-188726/1999 (Nippon Shokubai Co., Ltd.). However, their necessity becomes less as the solid component concentration of the hydropolymer gets higher.

The weight-average particle diameter of the disintegrated hydropolymer as obtained by the disintegrating means according to the present invention is favorably not larger than 100 mm, more favorably not larger than 10 mm, still more favorably not larger than 3 mm, most favorably not larger than 1 mm. It is ideal that the disintegration can be made even into the particle diameters of end products in a hydropolymer state.

The residual monomer content of the disintegrated particulate hydropolymer as obtained by the disintegrating means according to the present invention is not especially limited, but is not more than 3,000 ppm favorably for prevention of the residual monomers from flying about in such as the subsequent drying step. According to uses, the residual monomer content is favorably not more than 1,000 ppm, more favorably not more than 500 ppm, most favorably not more than 300 ppm. Particularly in the case where the particulate hydropolymer is intactly used for sanitary articles such as disposable diapers, the residual monomer content is favorably not more than 1,000 ppm, more favorably not more than 500 ppm.

It is favorable that the disintegrated hydropolymer (particulate hydropolymer) as obtained by the disintegrating means according to the present invention has a solid component concentration in the range of 55 to 82 weight %, a residual monomer content of not more than 1,000 ppm, and a weight-average particle diameter of not larger than 3 mm.

Incidentally, the disintegrated hydropolymer (particulate hydropolymer) having a solid component concentration in the range of 55 to 82 weight %, a residual monomer content of not more than 1,000 ppm, and a weight-average particle diameter of not larger than 3 mm, according to the present invention, does not include those which are obtained by adding water to a hydropolymer which has once got into a dry state (solid component concentration=not less than 83 weight %).

In the production process according to the present invention, the disintegrated hydropolymer may be dried. The drying method is not especially limited, but favorable examples thereof include drying methods in which the material is sufficiently brought into contact with hot air or a heat transfer surface while being moved, such as agitation drying methods, fluidized-bed drying methods, and pneumatic drying methods.

In the production process according to the present invention, how to subsequently treat the disintegrated hydropolymer (particulate hydropolymer) can be selected from among the following methods:

(1) The particulate hydropolymer is intactly made into manufactured goods, namely, intactly provided to uses such as sanitary articles or agricultural and horticultural uses. In order to afford the fluidity to the particles, they may be mixed with finely-particulate inorganic substances (e.g. bentonite, zeolite, silicon dioxide).

(2) The particulate hydropolymer is mixed with and allowed to react with a surface-crosslinking agent, and then made into manufactured goods still in a water-containing state. This method needs no energy for vaporization of water. In order to afford the fluidity to the particles, they may be mixed with finely-particulate inorganic substances (e.g. bentonite, zeolite, silicon dioxide).

(3) The particulate hydropolymer is mixed with and allowed to react with a surface-crosslinking agent, and dried, and then made into manufactured goods. In this method, the heating energy for drying can serve as energy for the surface-crosslinking reaction, too.

(4) The particulate hydropolymer is dried and then intactly made into manufactured goods.

(5) The particulate hydropolymer is dried, and then pulverized, and then classified, and then made into manufactured goods.

(6) The particulate hydropolymer is dried, and then pulverized, and then classified, and then surface-crosslinked, and then made into manufactured goods.

Because it has become possible to obtain the particulate hydropolymer by disintegrating the hydropolymer having a solid component concentration of 55 to 82 weight % which has so far been difficult to disintegrate, the following have newly become possible.

1) The above methods (1) to (3) becomes possible.

2) It is possible to use the aforementioned drying methods in which the material is sufficiently brought into contact with hot air or a heat transfer surface while being moved and which are therefore good in thermal efficiency (such as agitation drying methods, fluidized-bed drying methods, and pneumatic drying methods), but has so far been difficult to use as drying methods for a hydropolymer having a solid component concentration of lower than 55 weight % unless a material having a mold-releasing function such as a surfactant is added thereto.

3) Because the disintegration of the polymer can be carried out in a water-containing state, almost no fine powder is generated, so a particulate hydropolymer with a low fine-powder content is obtained.

Another favorable example of the production process, according to the present invention, is a process for producing a water-absorbent resin which comprises the step of polymerizing an aqueous solution of water-absorbent resin-forming monomers including acrylic acid and/or its salt as major components, wherein:

(1) the polymerization step produces a hydropolymer having a solid component concentration in the range of 55 to 82 weight %;

and wherein the process further comprises the following steps:

(2) a disintegration step for disintegrating the hydropolymer, which has a solid component concentration in the range of 55 to 82 weight %, into particles of which the weight-average diameter is not larger than 10 mm; and (3) a drying step for increasing the solid component concentration in the disintegrated hydropolymer by not less than 3%. The inclusion of these three steps makes it possible to provide a process by which a water-absorbent resin with excellent performance is produced at a low cost and further to provide by reasonable steps the following materials: a base polymer exhibiting a high absorption capacity without load and having a low extractable content; and a surface-crosslinked water-absorbent resin exhibiting a high absorption capacity under a load.

The present invention further provides a novel water-absorbent resin which well functions in uses such as sanitary articles, and is not bulky and is easily decomposed into linear polymers when being disposed of after being used.

As to conventional methods for disposing of water-absorbent resin-containing sanitary articles such as disposable diapers and sanitary napkins after being consumed by users, examples thereof include: (1) combustion; (2) landfill; (3) combustion after volume reduction treatment; (4) putting down flush toilets; (5) conversion into compost; and (6) others. Many studies and investigations are made about influences of waste water-absorbent resins upon the environment, and it is reported that the influences are on levels which do not matter. However, in the case where used sanitary articles are embedded into soil, water-absorbent resins absorb water in soil to swell much and are therefore considered to occupy places and spaces for wastes. Such things have not yet mattered, but are desired to also be taken into consideration in future, and it is desirable therefor that the water-absorbent resins become soluble or decompose in the environment.

Thus, many studies are made about biodegradable water-absorbent resins.

For example, they are reported in JP-A-0255896/1999 (Mitsui Chemical Corporation), JP-A-114803/2001 (Yunichika), JP-A-059820/1996 (Nippon Shokubai Co., Ltd.), JP-A-196901/1996 (Nippon Shokubai Co., Ltd.), JP-A-089796/1996 (Nippon Shokubai Co., Ltd.), JP-A-124754/1997 (Nippon Shokubai Co., Ltd.), and JP-A-216914/1997 (Nippon Shokubai Co., Ltd.). However, these are made into manufactured goods of which the prices are high because of their expensive raw materials and complicated production processes. In addition, they are inferior to acrylic acid-based water-absorbent resins also in respect to performance. Therefore, in the present circumstances, they have not yet been put to practical use.

JP-A-104929/2001 (Nippon Asahi Kiko Sale) proposes a process for volume reduction treatment of used disposable diapers, and water-absorbent resins are desired to become less bulky after being used.

Sanitary articles which contain water-absorbent resins and can be put down flush toilets were also devised (JP-A-210166/1994 and U.S. Pat. No. 5,415,643 (Kimbery-Clerk)). Because the water-absorbent resins swell in drainpipes, the possibility that the drainpipes might be clogged up becomes high. Therefore, water-absorbent resins are desired to become soluble or decompose when they have been put down flush toilets.

In addition, waste water-absorbent resins involved by the process for producing water-absorbent resins are thought to be disposed of by combustion, but there are also attempts to usefully utilize the waste water-absorbent resins. For example, U.S. Pat. No. 6,143,820 (Dow) discloses an attempt to decompose an acrylic acid-based water-absorbent resin into a linear polymer and to make good use of this linear polymer as a dispersant, a scale inhibitor, or a detergent additive.

The present invention provides a novel water-absorbent resin to solve these problems.

Specifically, this water-absorbent resin, according to the present invention, is obtained by a process including the step of polymerizing an aqueous solution of water-absorbent resin-forming monomers including acrylic acid and/or its salt as major components, and has the following properties:

(1) 20 (g/g)$\leqq$absorption capacity without load (GV)$\leqq$60 (g/g);

(2) absorption capacity under a load (AAP)$\geqq$20 (g/g); and (3) absorption capacity without load (GV)×solubilization residue ratio (%)$\leqq$1,200 ((g/g) %).

The above absorption capacity without load (GV) is favorably in the range of 25 to 55 (g/g), more favorably 25 to 50 (g/g). In the case where the absorption capacity without load (GV) is less than 20 (g/g), there are uneconomical disadvantages. In the case where the absorption capacity without load (GV) is more than 60 (g/g), there are disadvantages in that the gel strength is not obtained on a practical use level.

The above absorption capacity under a load (AAP) is favorably not less than 25 (g/g), more favorably not less than 30 (g/g), still more favorably not less than 35 (g/g). In the case where the absorption capacity under a load (AAP) is less than 20 (g/g), there are disadvantages in that no favorable performance is exhibited when the resultant water-absorbent resin is used for sanitary articles in a high concentration.

The value of the above absorption capacity without load (GV)×solubilization residue ratio (%) is favorably not more than 1,000 ((g/g) %), more favorably not more than 800 ((g/g) %), still more favorably not more than 600 ((g/g) %). In the case where this value is more than 1,200 ((g/g) %), there are disadvantages in that the resultant water-absorbent resin is difficult to decompose and solubilize.

A specific process for producing the above water-absorbent resin comprises the step of polymerizing an aqueous solution of water-absorbent resin-forming monomers including acrylic acid and/or its salt as major components, wherein:

(1) the aqueous solution has a monomer component concentration of not less than 50 weight %; and (2) an internal-crosslinking agent is used in a ratio of not larger than 0.02 mol % to the entirety of the water-absorbent resin-forming monomers;

and wherein the process further comprises the steps of:

(3) surface-crosslinking the water-absorbent resin; and (4) adding a chelating agent to the water-absorbent resin in a ratio of not less than 10 ppm thereto.

More specifically, the monomer component concentration in the aqueous solution needs not to be less than 50 weight %, and is favorably in the range of 53 to 70 weight %. The ratio of the internal-crosslinking agent to the entirety of the water-absorbent resin-forming monomers needs not to be larger than 0.02 mol %, and is favorably not larger than 0.01 mol %, more favorably not larger than 0.005 mol %. Furthermore, the water-absorbent resin needs to be surface-crosslinked, and the GV of the surface-crosslinked resin is favorably not larger than 80%, more favorably not larger than 70%, still more favorably not larger than 60%, most favorably not larger than 50%, of that of the base polymer.

In the case where a water-absorbent resin is used for sanitary articles, such a water-absorbent resin as decomposes when being used is of no practical use. Therefore, the addition of the chelating agent to the water-absorbent resin is needed. The addition of the chelating agent may be carried out in any step of the process for producing the water-absorbent resin. In the case where the amount of the chelating agent as added is less than 10 ppm, the effects are poor. The amount of the chelating agent as added is favorably not less than 20 ppm.

Effects and Advantages of the Invention

The present invention can provide by reasonable steps the following materials: a base polymer exhibiting a high absorption capacity without load and having a low extractable content; and a surface-crosslinked water-absorbent resin exhibiting a high absorption capacity under a load.

Because the water-absorbent resin obtained by the present invention exhibits the above effects, this water-absorbent resin is useful for various purposes, for example, as follows: articles contacting human bodies, such as sanitary articles (e.g. disposable diapers for children and adults, sanitary napkins, and adult incontinent products); water-retaining materials for plants and soil; sealing materials for electric wires and optical cables; and sealing materials for engineering works or constructions.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited thereto. Incidentally, in the examples, unless otherwise noted, the unit "part(s)" denotes that by weight.

(Measurement of Absorption Capacity without Load (GV)):

First, 0.2 g of water-absorbent resin was uniformly placed into a nonwoven-fabric-made bag (60 mm×60 mm), and then the bag was immersed into a 0.9 weight % aqueous sodium chloride solution (physiological saline solution). Thirty minutes later, the bag was drawn up and then drained at 250×9.81 m/s$^2$ (250 G) for 3 minutes with a centrifugal separator, and the resultant weight W1 (g) of the bag was then measured. On the other hand, the same procedure was carried out without the water-absorbent resin, and the resultant weight W0 (g) was measured. Thus, the GV (absorption capacity without load) was calculated from these weights W1 and W0 in accordance with the following equation:

$$GV(g/g) = [\{\text{weight } W1(g) - \text{weight } W0(g)\}/(\text{weight}(g) \text{ of water-absorbent resin})] - 1$$

In addition, as to the hydropolymer, its GV measurement was carried out in the same way as that for the water-absorbent resin except that: 0.2 g in terms of solid content of the hydropolymer was used; the time of the immersion in the physiological saline solution was 24 hours; and the GV calculation involved a correction based on the solid content.

(Measurement of Extractable Content and Neutralization Ratio):

An amount of 184.3 g of a 0.9 wt % aqueous NaCl solution (physiological saline solution) was weighed out into a plastic container of a capacity of 250 ml with a lid, and then 1.00 g of water-absorbent resin was added to this aqueous solution, and then they were stirred together for 16 hours, whereby extractable components were extracted from the resin. The resultant dispersion was filtered with filter paper, and 50.0 g of the resultant filtrate was weighed out as a measurement solution.

First of all, the physiological saline solution was titrated alone with a 0.1 N aqueous NaOH solution until pH reached 10, and then with a 0.1 N aqueous HCl solution until pH reached 2.7, thus obtaining blank titration amounts ([bNaOH] ml and [bHCl] ml).

The same titration procedure as the above was carried out for the measurement solution, thereby determining its titration amounts ([NaOH] ml and [HCl] ml).

For example, in the case of a water-absorbent resin comprising acrylic acid and its sodium salt, the extractable content and the neutralization ratio of this water-absorbent resin can be calculated from the weight-average molecular weight of the water-absorbent resin and the titration amounts, as determined by the above procedures, in accordance with the following calculation formula:

$$\text{Neutralization ratio(mol \%)} = \{1 - ([\text{NaOH}] - [b\text{NaOH}])/([\text{HCl}] - [b\text{HCl}])\} \times 100$$

$$\text{Extractable content(weight \%)} = 0.1 \times Mw \times 184.3 \times 100 \times ([\text{HCl}] - [b\text{HCl}])/1{,}000/1.0/50.0$$

wherein $Mw = 72.06 \times (1 - \text{neutralization ratio}/100) + 94.04 \times \text{neutralization ratio}/100$ In addition, as to the hydropolymer, its extractable content measurement was carried out in the same way as that for the water-absorbent resin except that: 1.00 g in terms of solid content of the hydropolymer was used; the time of the immersion in the physiological saline solution was 24 hours; and the extractable content calculation involved a correction based on the solid content.

(GEX Value):

When the GV value and the extractable content of the base polymer are denoted by y (g/g) and x (weight %) respectively, the GEX value is defined by the following equation:

$$GEX \text{ value} = (y - 15)/\ln(x)$$

wherein: $\ln(x)$ is a natural logarithm of x.

The GEX value is an index for denoting by one parameter an evaluation of regarding a low extractable content for GV value as good and a high extractable content for GV value as bad in relations between the GV value and the extractable content. The larger this GEX value is, the higher the performance is.

(Measurement of Residual Monomer Content):

First, 0.5 g of water-absorbent resin was added to 1,000 g of deionized water to carry out extraction under stirring for 2 hours. Then, the resultant swollen gelled water-absorbent resin was filtered off with filter paper, and then the residual monomer content of the resultant filtrate was analyzed by liquid chromatography. On the other hand, a calibration curve which was obtained by analyzing a monomer standard solution of an already known concentration in the same way as the above was taken as an external standard. Therefrom, the residual monomer content of the water-absorbent resin was determined in consideration of the dilution magnification of the filtrate.

In addition, as to the hydropolymer, its residual monomer content measurement was carried out in the same way as that for the water-absorbent resin except that: 0.5 g in terms of solid content of the hydropolymer was used; the time of the immersion in the physiological saline solution was 24 hours; and the residual monomer content calculation involved a correction based on the solid content.

(Measurement of Solid Component Concentration in Hydropolymer):

A bit of a portion of the hydropolymer as got out of the polymerization reactor was cut off and then quickly cooled and then quickly divided into fine pieces with scissors. Next, 5 g of the hydropolymer as finely divided in this way was placed into a Petri dish and then dried in a drying oven of 180° C. for 24 hours to calculate the solid component concentration in the hydropolymer. As to a particulate hydropolymer, the solid component concentration therein was calculated by placing 5 g of sample into a Petri dish and then drying it in a drying oven of 180° C. for 24 hours.

(Calculation of Concentration Ratio):

Calculated is a ratio (concentration ratio) between a solid component concentration in the hydropolymer as formed by polymerization and a solid component concentration in the aqueous monomer solution. Incidentally, the solid components in the aqueous monomer solution are monomers and other additives, and do not include water or solvents. For example, in the case where the solid component concentration in the aqueous monomer solution is 40 weight % and where the solid component concentration in the formed hydropolymer is 48 weight %, the concentration ratio is 48/40=1.20.

(Measurement of Absorption Capacity Under Load (AAP)):

First, 0.9 g of water-absorbent resin is uniformly spread on a stainless metal gauze of 400 mesh (mesh opening size: 38 μm) as attached by fusion to the bottom of a plastic supporting cylinder with an inner diameter of 60 mm. Next, a piston and a load are mounted in sequence on the above water-absorbent resin, wherein the piston has an outer diameter of only a little smaller than 60 mm and makes no gap with the wall face of the supporting cylinder, but is not hindered from moving up and down, and wherein the total weight of the piston and the load is adjusted to 565 g so that a load of 20 g/cm$^2$ (corresponding to 1.96 kPa) can uniformly be applied to the water-absorbent resin. Then, the weight (Wa) of the resultant set of measurement apparatus is measured.

A glass filter plate of 90 mm in diameter is mounted inside a Petri dish of 150 mm in diameter, and a 0.9 weight % aqueous NaCl solution is added up to the same level as the surface of the glass filter plate, on which filter paper of 90 mm in diameter is then mounted so that its entire surface will be wetted, and further, an excess of liquid is removed.

The above set of measurement apparatus is mounted on the above wet filter paper, thereby allowing the water-absorbent resin to absorb the liquid under load. Then, 1 hour later, the set of measurement apparatus is removed by being lifted to measure its weight (Wb) again.

The absorption capacity under load (AAP) is determined from the following equation:

$$AAP(g/g)=(Wb-Wa)/0.9$$

(Measurement of Temperature of Polymerization System):

A PC card type data-collecting system, NR-1000 produced by Keyence Co., Ltd., was used to measure the temperature of a system exhibiting a rapid change of temperature. A thermocouple was put in the central portion of the polymerization system to measure its temperature at a sampling period of 0.1 second. The polymerization initiation temperature and the peak temperature (highest temperature) were read from the resultant temperature-time chart.

(Polymerization Time):

Measured is a period of time of from completion of the polymerization initiation conditions following the charge of the aqueous monomer solution into a polymerization reactor (from initiation of irradiation of light in the case where the at least one photoinitiator is used; or from charge of the aqueous monomer solution and a polymerization initiator into a polymerization reactor in the case where no photoinitiator is used) till attainment to the peak temperature. Namely, the total of (induction period)+(period of time of from polymerization initiation till peak temperature) is measured.

(Ratio of Temperature Rising During Polymerization):

The ratio of temperature rising during the polymerization is a ratio of $\Delta T$ (difference between the highest temperature during the polymerization and the polymerization initiation temperature; ° C.), as observed for the polymerization system, to theoretical $\Delta T$ (° C.) as follows:

$$\text{Ratio of temperature rising during polymerization}=(\text{observed }\Delta T(° C.))/(\text{theoretical }\Delta T(° C.))$$

wherein: theoretical $\Delta T$ (° C.)=(monomer mol)×(1.85 kcal/mol)/(solid components (kg) in aqueous monomer solution×0.5 (kcal/° C./kg)+water (kg) in aqueous monomer solution×1.0 (kcal/° C./kg))

(Measurement of Dissolved Oxygen Content of Aqueous Monomer Solution):

A measurement apparatus (DO meter UD-1 model produced by Central Science Co., Ltd.) was used to measure the dissolved oxygen content of the prepared aqueous monomer solution when its liquid temperature was 50° C. by icing the solution while gently stirring it so as not to mingle bubbles thereinto under a nitrogen atmosphere.

(Increase of Neutralization Ratio):

The difference between the neutralization ratio of the base polymer and that of the monomers is denoted by points. For example, in the case where the neutralization ratio of the base polymer is 65 mol % and where that of the monomers is 60 mol %, the increase of the neutralization ratio is 5 points.

(Measurement of Expansion Magnification During the Polymerization):

There is a case where the polymerization system expands, because water boils during the polymerization. Scales are made lengthways and widthways at intervals of 1 cm in the polymerization reactor, and the volume of the polymerization system is determined by measuring its size with the eye when the polymerization system has expanded to the maximum during the polymerization. Then, the ratio of the determined maximum volume of the polymerization system to the volume of the aqueous monomer solution is calculated as follows:

$$\text{Expansion magnification(times)during the polymerization}=(\text{maximum volume of polymerization system})/(\text{volume of aqueous monomer solution})$$

(Measurement of Particle Diameter Distribution of Particulate Hydropolymer):

About 300 g of particulate hydropolymer is placed into a plastic bag, and thereto 1 g of Aerosil R-972 (hydrophobic fine particles of silicon dioxide, produced by Nippon Aerosil Co., Ltd.), and they are mixed together and well disintegrated by hand. The resultant disintegrated product is shaken with a standard screen of 20 cm in inner diameter and a Ro-Tap type screen shaker for 10 minutes. Depending on the water content of the particulate hydropolymer, there is a case where the particulate hydropolymer aggregates so much when being screen-shaken as to make it difficult to precisely measure the particle diameter distribution. Therefore, the measurement is carried out by adding the Aerosil R-972 to the particulate hydropolymer.

(Solubilization Test Method):

The water-absorbent resin basically has a form of a crosslinked polymer as produced by crosslinking of a water-soluble polymer. This solubilization test method is a test method for evaluating how easily this water-absorbent resin decomposes when exposed to decomposing conditions. Accordingly, according to decomposing conditions to which the water-absorbent resin is actually exposed, the tendency does not necessarily give agreement with the result of this test method.

In this test method, the water-absorbent resin is decomposed by washing such as extractable components off with water to obtain a gel comprising a crosslinked polymer itself, and then irradiating it with ultraviolet rays. This evaluation method gives a quantitative index for the ease of decomposition of the crosslinked polymer itself. The procedure therefor is as follows.

1. The water-absorbent resin is classified into the particle diameter range of 300 to 850 µm.
2. Next, 0.500 g of the classified resin is dispersed into 1,000 cc of ion-exchanged water in a PP (polypropylene)-made cylindrical container and thereby swollen with the ion-exchanged water. This operation is carried out under stirring with a magnetic stirrer (600 rpm).
3. The stirring is continued at normal temperature for 2 hours.
4. The resultant dispersion is poured onto a circular standard sieve (mesh opening size=300 µm) of 20 cm in diameter, and water is drained off by tapping the sieve by hand. Then, the gel as left on the sieve is returned into the PP-made cylindrical container, and then ion-exchanged water is added thereto till the entire contents of the container amounts to 1,000 cc, and then the stirring is carried out again for 2 hours.
5. This washing operation is carried out three times, and then the water-drained gel is placed into a glass Petri dish of 153 mm in diameter.
6. A mercury lamp, H400BL (produced by Toshiba Lightech Co., Ltd.), is fitted to a reflective shade, SN4042A (produced by Toshiba Lightech Co., Ltd.), and then connected to a mercury lamp stabilizer, H4T1B51 (produced by Iwasaki Denki Co., Ltd.), and then lighted. The above Petri dish is put on a face located 18 cm below the lower end of the mercury lamp. The irradiation energy in a place 18 cm just under the mercury lamp is 40 mW/cm$^2$ as measured with a ultraviolet integration actinometer, UIT-150 (produced by Ushio Denki Co., Ltd.).
7. The gel on the Petri dish is irradiated by the mercury lamp for 30 minutes.
8. After the irradiation, the contents of the Petri dish is returned into the PP-made cylindrical container, and then ion-exchanged water is added thereto till the entire contents of the container amounts to 1,000 cc, and then the stirring is carried out for 2 hours. The washing operation is carried out three times in the same way as of the above operations 4 and 5.
9. The gel as left on the standard sieve (mesh opening size=300 µm) is placed into a glass Petri dish of 153 mm in diameter and then solidified by drying in a drying oven of 180° C. for 5 hours to determine a solid content (a).
10. Separately, the above operations 1 to 5 are carried out to obtain a gel, and its solid content (b) (before UV irradiation) is determined in the same way as of the above operation 9.
11. The solubilization residue ratio is calculated from solubilization residue ratio=a/b×100(%).

EXAMPLE 1

A stainless beaker of an inner diameter of 10 cm was fitted with a polystyrene foam-made lid as equipped with a nitrogen-introducing tube, an exhaust tube, and a thermometer. Furthermore, the whole stainless beaker was covered with polystyrene foam which is a heat insulator. Then, the beaker was charged with 40.6 g of a 80 weight % aqueous acrylic acid solution in which 0.09 g of polyethylene glycol diacrylate (number-average molecular weight=478) was dissolved. While stirring was being done with a magnetic stirrer, neutralization was carried out by adding a product as obtained by diluting 28.2 g of a 48 weight % aqueous sodium hydroxide solution with 31.0 g of ion-exchanged water. As a result, the internal temperature reached 90° C. The neutralization ratio of the resultant aqueous monomer solution was 75 mol %. Then, while nitrogen was introduced, 0.45 g of a 10 weight % aqueous sodium persulfate solution was added. Immediately thereafter, polymerization was initiated (polymerization initiation temperature=90° C.), and then the polymerization system reached the polymerization peak temperature (108° C.) while emitting water vapor. The time as needed from the addition of the aqueous sodium persulfate solution till the polymerization peak temperature, that is, the polymerization time, was 2 minutes. After the attainment to the polymerization peak temperature, the heat insulating state was still retained for 5 minutes. The resultant hydropolymer was got out and then divided into fine pieces with scissors. As a result, 7 minutes were needed from adding the polymerization initiator till getting out the hydropolymer. The finely divided hydropolymer was dried with a hot-air oven of 170° C. for 40 minutes and then pulverized with a laboratory pulverizer. Next, the pulverized product was classified with screen meshes of the mesh opening sizes of 600 µm and 300 µm, thus obtaining a base polymer (1), most of which had particle diameters of 300 to 600 µm.

The base polymer (1) had a GV of 47 g/g, an extractable content of 10 weight %, a residual monomer content of 300 ppm, and a neutralization ratio of 77 mol %. In addition, the finely divided hydropolymer had a solid component concentration of 48 weight %. The concentration ratio was 1.20.

Next, 100 parts of the base polymer (1) was mixed with a surface-crosslinking agent composition solution comprising 0.05 part of ethylene glycol diglycidyl ether, 1 part of propylene glycol, and 2 parts of water, and then the resultant mixture was heated in a drying oven of 80° C. for 40 minutes, thus obtaining a surface-crosslinked water-absorbent resin (1) of which the surface vicinity had been crosslinked.

The surface-crosslinked water-absorbent resin (1) had a GV of 39 g/g and an AAP of 38 g/g.

The results are shown in Table 1.

Figure 2:
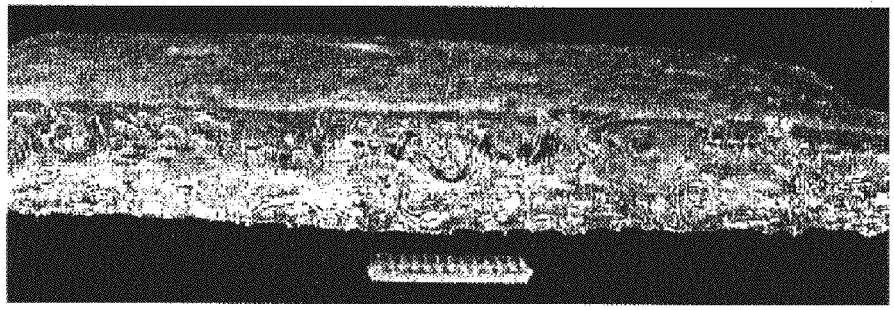
FIG. 2 is a side view photograph of the hydropolymer as obtained in Example 1.

In addition, a side view photograph of the hydropolymer as obtained in Example 1 is shown in FIG. 2. The lateral bar below the center of this photograph of FIG. 2 is 1 cm long.

COMPARATIVE EXAMPLE 1

A polymerization apparatus, as prepared by fitting the same stainless beaker as that used in Example 1 with a polystyrene foam-made lid as equipped with a nitrogen-introducing tube, an exhaust tube, and a thermometer, was immersed into a water bath of 20° C. Then, the polymerization apparatus was charged with the same aqueous monomer solution as that used in Example 1. Then, while nitrogen was introduced, 0.45 g of a 10 weight % aqueous sodium persulfate solution and 0.45 g of a 0.1 weight % aqueous L-ascorbic acid solution were added. Seven minutes later, polymerization was initiated. The polymerization was carried out while the polymerization system was cooled with the water bath of 20° C., so that the polymerization system reached the polymerization peak temperature of 60° C. Thereafter, heating was carried out for 30 minutes by raising the temperature of the water bath to 70° C.

Thereafter, the resultant hydropolymer was got out and then divided into fine pieces with scissors. As a result, 62 minutes were needed from adding the polymerization initiator system till getting out the hydropolymer. The finely divided hydropolymer was dried with a hot-air oven of 170° C. for 40 minutes and then pulverized with a laboratory pulverizer. Next, the pulverized product was classified with screen meshes of the mesh opening sizes of 600 μm and 300 μm, thus obtaining a comparative base polymer (1), most of which had particle diameters of 300 to 600 μm.

The comparative base polymer (1) had a GV of 36 g/g, an extractable content of 11 weight %, a residual monomer content of 300 ppm, and a neutralization ratio of 75 mol %. In addition, the finely divided hydropolymer had a solid component concentration of 42 weight %. The concentration ratio was 1.05.

Next, 100 parts of the comparative base polymer (1) was mixed with a surface-crosslinking agent composition solution comprising 0.05 part of ethylene glycol diglycidyl ether, 1 part of propylene glycol, and 2 parts of water, and then the resultant mixture was heated in a drying oven of 80° C. for 40 minutes, thus obtaining a comparative surface-crosslinked water-absorbent resin (1) of which the surface vicinity had been crosslinked.

The comparative surface-crosslinked water-absorbent resin (1) had a GV of 28 g/g and an AAP of 26 g/g.

The results are shown in Table 1.

Between Example 1 and Comparative Example 1, such as the composition of the monomers and the amount of the initiator are the same, and only the polymerization initiation temperature (90° C. in Example 1 and 20° C. in Comparative Example 1) and the subsequent temperature are different. Example 1 is superior in respect to the performance of the resultant base polymer and water-absorbent resin. Although the reason therefor is not clear, the present inventors' inference is as follows.

The polymerization initiation at 20° C. results in the deterioration of the GV, because the polymer as formed in the stage of a low polymerization conversion has too high a molecular weight, and because much of the crosslinking agent is consumed in the initial stage of the polymerization (reference: Crosslinker Reactivity and the Structure of Superabsorbent Gels, D. J. Arriola et al., J. Appl. Polym. Sci. 63, 439-451 (1997)). On the other hand, as to the polymerization initiation at 90° C., the deterioration of the GV is suppressed, because the molecular weight of the polymer as formed in the stage of a low polymerization conversion is suppressed.

EXAMPLE 2

An aqueous monomer solution having a monomer concentration of 50 weight % and a neutralization ratio of 65 mol % was prepared by mixing together 83.5 parts of acrylic acid, 62.1 parts of a 48.5 weight % aqueous NaOH solution, 54.3 parts of ion-exchanged water, 0.11 part of polyethylene glycol diacrylate (number-average degree of polymerization of ethylene oxide=8) as a crosslinking agent, and 0.01 part of 2-hydroxy-2-methyl-1-phenyl-propan-1-one as an initiator. This solution was deaerated under a nitrogen atmosphere for 30 minutes and then poured into a Teflon-coated stainless container having a bottom of 200×260 mm, wherein the container was put on a hot plate (NEO HOTPLATE HI-1000 produced by Inouchi Seieido Co., Ltd.) of 90° C. and nitrogen gas was being introduced into the container. When the temperature of the aqueous monomer solution rose to 60° C., this solution was irradiated with ultraviolet rays by four black light fluorescent lamps (FL6BLB produced by Toshiba Lightech Co., Ltd.) for 10 minutes (quantity of light=900 mJ/cm$^2$), thus obtaining a hydropolymer of about 3 mm in thickness. The polymerization initiation temperature was 60° C., and the highest temperature was 110° C. during the polymerization, and the polymerization time was 80 seconds, and the expansion magnification was 5 times. Immediately after the end of the ultraviolet irradiation, the hydropolymer was got out and then cut into fine pieces with scissors and then dried with hot air of 170° C. for 30 minutes and then pulverized with a laboratory pulverizer. Next, the pulverized product was classified with screen meshes of the mesh opening sizes of 600 μm and 300 μm, thus obtaining a base polymer (2), most of which had particle diameters of 300 to 600 μm.

The base polymer (2) had a GV of 58 g/g, an extractable content of 16 weight %, a neutralization ratio of 68 mol %, and a residual monomer content of 2,200 ppm. In addition, the hydropolymer had a solid component concentration of 60 weight %. The concentration ratio was 1.20.

Next, 100 parts of the base polymer (2) was mixed with a surface-crosslinking agent composition solution comprising 0.05 part of ethylene glycol diglycidyl ether, 1 part of propylene glycol, and 2 parts of water, and then the resultant mixture was heated in a drying oven of 80° C. for 40 minutes, thus obtaining a surface-crosslinked water-absorbent resin (2) of which the surface vicinity had been crosslinked.

The surface-crosslinked water-absorbent resin (2) had a GV of 42 g/g and an AAP of 36 g/g.

The results are shown in Table 1.

EXAMPLE 3

A solution (A) was prepared by mixing together 139.5 g of acrylic acid, 0.09 g of polyethylene glycol diacrylate (number-average molecular weight=478), and 0.02 g of 2-hydroxy-2-methyl-1-phenyl-propan-1-one. In addition, an aqueous NaOH solution (B) was prepared by diluting 95.8 g of a 48.5 weight % aqueous NaOH solution with 61.2 g of ion-exchanged water and then adding 0.02 g of diethylenetriaminepentaacetic acid pentasodium salt to the resultant dilution. These solutions were deaerated under a nitrogen atmosphere for 30 minutes. Then, while stirring was carried out with a magnetic stirrer, the solution (A) was added to the solution (B) in an open system all at once to mix them together. A deposit was seen in the initial stage of the mixing step, but instantly dissolved to give an aqueous monomer solution (monomer concentration=55 weight % and neutralization ratio=60 mol %) of which the liquid temperature had risen to about 90° C. due to a heat of neutralization and a heat of dissolution. Furthermore, 0.58 g of a 10 weight % aqueous sodium persulfate solution was added to this aqueous monomer solution, and then the resultant mixture was stirred for several seconds and then immediately poured into a stainless vat type container having a bottom of 200×260 mm (surface temperature=about 64° C.) in an open system (thickness of poured solution=about 5 mm), wherein the container was put on a hot plate of 90° C. and a silicone sheet was attached to the inner surface of the container. The stainless vat type container had the measurements of bottom=200×260 mm, top=560× 460 mm, height=140 mm, and was trapezoidal at the central section, and was open at the top. Immediately thereafter, ultraviolet irradiation was carried out with a black light mercury lamp (peak wavelength=352 nm, model No. H400BL, fitted within a projector MT-4020, wherein both the lamp and the projector were products of Toshiba Lightech Co., Ltd.) to initiate polymerization. While the polymerization system was emitting water vapor and expanding in all directions and foaming, the polymerization proceeded, and then the polymerization system shrank to almost the same size as the original. The resultant hydropolymer expanded to about 30 times at the maximum of the volume of the aqueous monomer solution according to the eye measurement and then shrank. When the hydropolymer expands, thin portions of the hydropolymer creep up tilt portions of the sides of the container and then, when the hydropolymer shrinks, the thin portions of the hydropolymer return toward their original places, but stop their movements as they are larger than the size of the bottom of the container. This expansion and shrinkage ended within about 1 minute and, when the UV irradiation for 2 minutes had been completed, the hydropolymer was got out. From the record of the change in temperature of the polymerization system, it was read that the polymerization initiation temperature was 88° C. and that the highest temperature was 111° C. The resultant hydropolymer was in a much wrinkly form either still in a foamed state or in a collapsed state, although it was according to sizes of bubbles. This hydropolymer was pulverized with VERTICAL PULVERIZER (model No. VM27-S produced by Orient Co., Ltd., screen mesh opening diameter=8 mm), thus obtaining a flowable particulate hydropolymer (3).

The hydropolymer (3) had a GV of 33 g/g, an extractable content of 6 weight %, and a residual monomer content of 600 ppm. In addition, the hydropolymer had a solid component concentration of 70 weight %. The concentration ratio was 1.27.

Subsequently, the hydropolymer (3) was dried with hot air of 170° C. for 20 minutes and then pulverized with a roll mill. Next, the pulverized product was classified with screen meshes of the mesh opening sizes of 850 μm and 150 μm, thus obtaining a base polymer (3), most of which had particle diameters of 150 to 850 μm, and which had a weight-average particle diameter of 360 μm.

The base polymer (3) had a GV of 48 g/g, an extractable content of 24 weight %, a neutralization ratio of 65 mol %, and a residual monomer content of 200 ppm. In addition, from observation of particles of the base polymer (3) with a microscope, it was found that: foaming occurred to the polymerization, but most of particles were in a noncrystalline form which contained no bubble nevertheless. The reason therefor seems to be that their bubble sizes were relatively large.

Next, 100 parts of the base polymer (3) was mixed with a surface-crosslinking agent composition solution comprising 0.03 part of ethylene glycol diglycidyl ether, 1 part of propylene glycol, and 5 parts of water, and then the resultant mixture was heated in a drying oven of 80° C. in a sealed container for 1 hour, thus obtaining a surface-crosslinked water-absorbent resin (3) of which the surface vicinity had been crosslinked.

The surface-crosslinked water-absorbent resin (3) had a GV of 34 g/g and an AAP of 35 g/g.

Furthermore, 100 parts of the base polymer (3) was mixed with a surface-crosslinking agent composition solution comprising 0.03 part of ethylene glycol diglycidyl ether, 1 part of propylene glycol, 3 parts of water, and 0.9 part of isopropyl alcohol, and then the resultant mixture was heated in a container as heated with an oil bath of 170° C. for 20 minutes, thus obtaining a surface-crosslinked water-absorbent resin (3a) of which the surface vicinity had been crosslinked.

The surface-crosslinked water-absorbent resin (3a) had a GV of 34 g/g and an AAP of 35 g/g.

The results are shown in Table 1.

Figure 3:
FIG. 3 is a side view photograph of the hydropolymer as obtained in Example 3.
Figure 4:
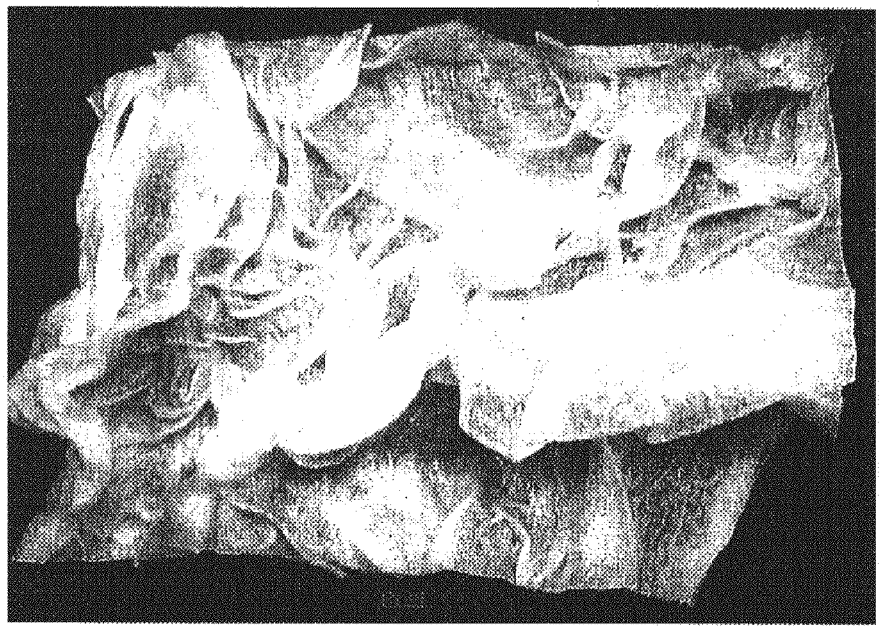
FIG. 4 is a top view photograph of the hydropolymer as obtained in Example 3.
Figure 5:
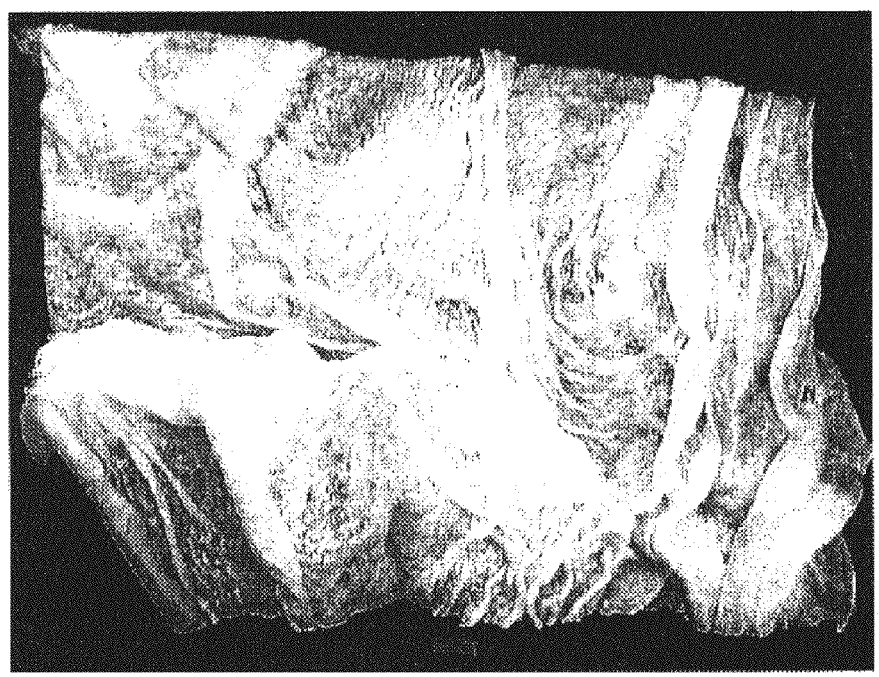
FIG. 5 is a bottom view photograph of the hydropolymer as obtained in Example 3.

In addition, a side view photograph, a top view photograph, and a bottom view photograph of the hydropolymer as obtained in Example 3 are shown in FIGS. 3, 4, and 5 respectively. The lateral bars below the centers of these photographs of FIGS. 3, 4, and 5 are 1 cm long.

EXAMPLE 4

The polymerization was carried out in the same way as of Example 3, and the evaporated water vapor was led with a fan and collected into a condenser (as cooled with ice water). The amount of an aqueous solution as collected by carrying out this procedure twice was 60 g, of which 3.4 weight % was acrylic acid.

The same procedure as of Example 3 was carried out except that this recovered water containing acrylic acid was substituted for most of ion-exchanged water as used in Example 3. The property values of the resultant base polymer (4) are shown in Table 1.

EXAMPLE 5

A base polymer (5) was obtained in the same way as of Example 3 except that 0.09 g of polyethylene glycol diacrylate (number-average molecular weight=478) (crosslinking agent) was replaced with 0.14 g of trimethylolpropane triacrylate (molecular weight=296). Then, 100 part of the resultant base polymer (5) was mixed with a surface-crosslinking agent composition solution comprising 1 part of propylene glycol, 0.5 part of 1,4-butanediol, 3 parts of water, and 1 part of isopropyl alcohol, and then the resultant mixture was heated at 210° C. for 40 minutes, thus obtaining a surface-crosslinked water-absorbent resin (5).

The results are shown in Table 1.

Figure 6:
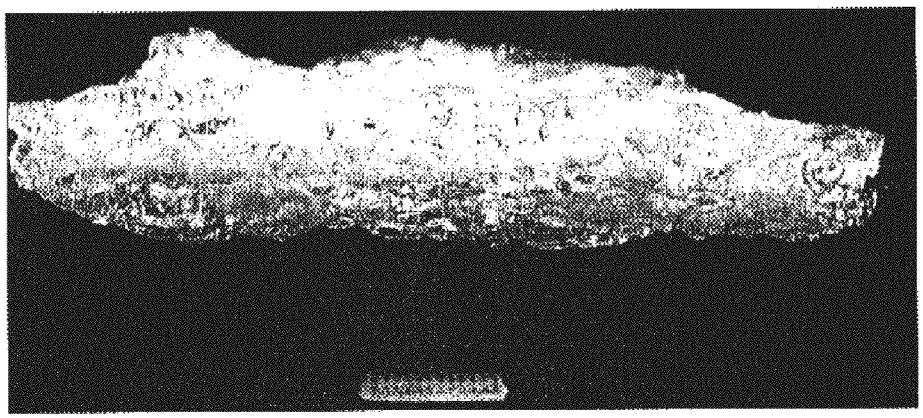
FIG. 6 is a side view photograph of the hydropolymer as obtained in Example 5.

In addition, a side view photograph of the hydropolymer as obtained in Example 5 is shown in FIG. 6. The lateral bar below the center of this photograph of FIG. 6 is 1 cm long.

EXAMPLE 6

An amount of 100 parts of the base polymer (5) as obtained in Example 5 was mixed with a surface-crosslinking agent composition solution comprising 3 parts of ethylene carbonate, 3 parts of water, and 1 part of isopropyl alcohol, and then the resultant mixture was heated at 210° C. for 40 minutes, thus obtaining a surface-crosslinked water-absorbent resin (6).

The results are shown in Table 1.

TABLE 1

|  | Example 1 | Example 2 | Example 3 | Example 4 | Example 5 | Example 6 | Comparative Example 1 |
|---|---|---|---|---|---|---|---|
| Concentration (weight %) in aqueous monomer solution | 40 | 50 | 55 | 55 | 55 | 55 | 40 |
| Neutralization ratio (mol %) of monomers | 75 | 65 | 60 | 60 | 60 | 60 | 75 |
| Polymerization initiation temperature (° C.) | 90 | 60 | 88 | 87 | 89 | 89 | 20 |
| Polymerization peak temperature (° C.) | 108 | 110 | 111 | 112 | 110 | 110 | 60 |
| ΔT (° C.) | 18 | 50 | 22 | 25 | 21 | 21 | 40 |
| Polymerization time (seconds) | 120 | 80 | 39 | 48 | 43 | 43 | 1,500 |
| Solid component concentration (weight %) in hydropolymer | 48 | 60 | 70 | 69 | 68 | 68 | 42 |
| Concentration ratio | 1.20 | 1.20 | 1.27 | 1.25 | 1.24 | 1.24 | 1.05 |
| GV (g/g) of base polymer | 47 | 58 | 48 | 50 | 29 | 29 | 36 |
| Extractable content (weight %) of base polymer | 10 | 16 | 24 | 23 | 4 | 4 | 11 |
| GEX value of base polymer | 13.9 | 15.5 | 10.4 | 11.2 | 10.1 | 10.1 | 8.8 |
| Neutralization ratio (mol %) of base polymer | 77 | 68 | 65 | 64 | 64 | 64 | 75 |
| Residual monomer content (ppm) | 300 | 2,200 | 200 | 300 | 270 | 270 | 300 |
| GV (g/g) of surface-crosslinked water-absorbent resin | 39 | 42 | 34 | — | 25 | 23 | 28 |
| AAP (g/g) of surface-crosslinked water-absorbent resin | 38 | 36 | 35 | — | 26 | 24 | 26 |

EXAMPLES 7 TO 10

Base polymers of Examples 7 to 10 (base polymers (7) to (10)) were obtained by carrying out the polymerization and the subsequent operation in the same way as of Example 3 except that the polymerization initiation temperature was changed by adjusting the temperature of the aqueous monomer solution and that of the hot plate. The results are compiled in Table 2.

Figure 7:
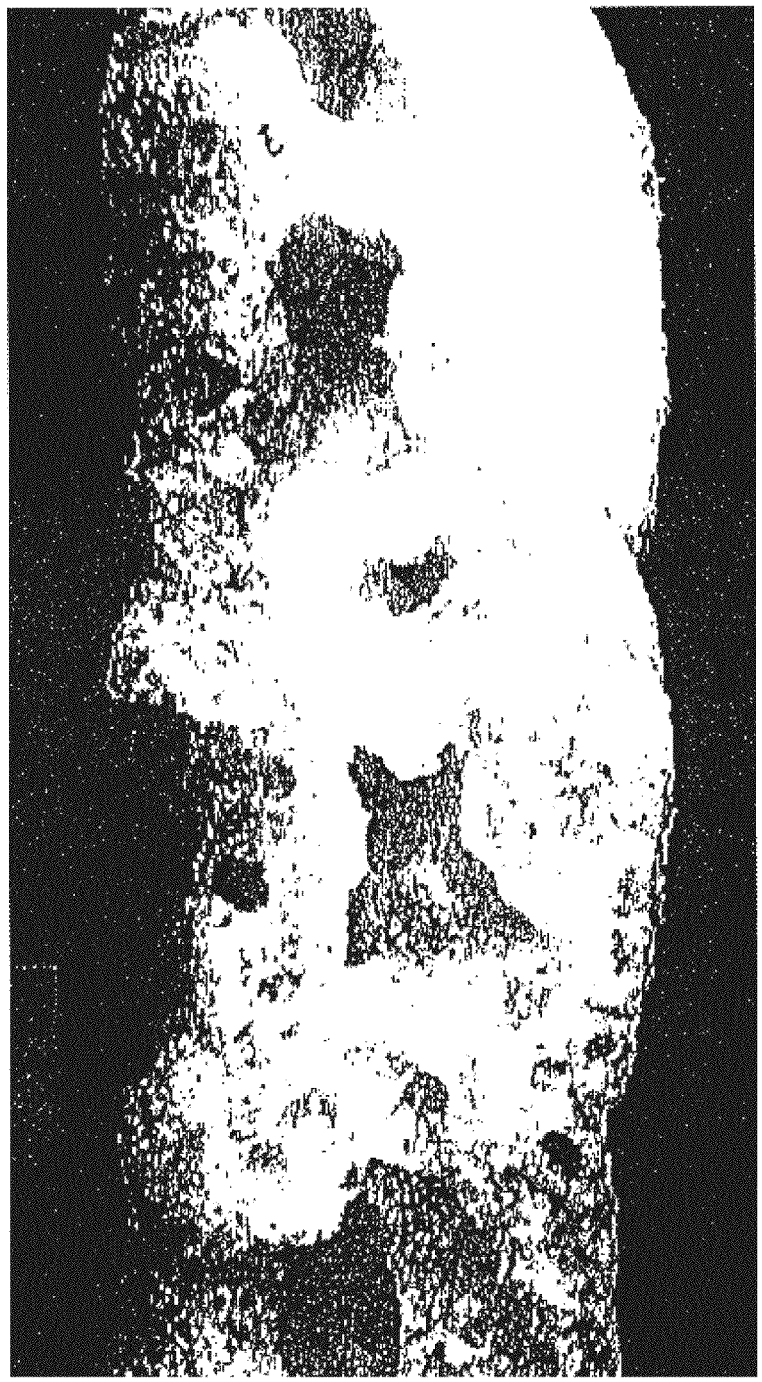
FIG. 7 is a side view photograph of the hydropolymer as obtained in Example 7.
Figure 8:
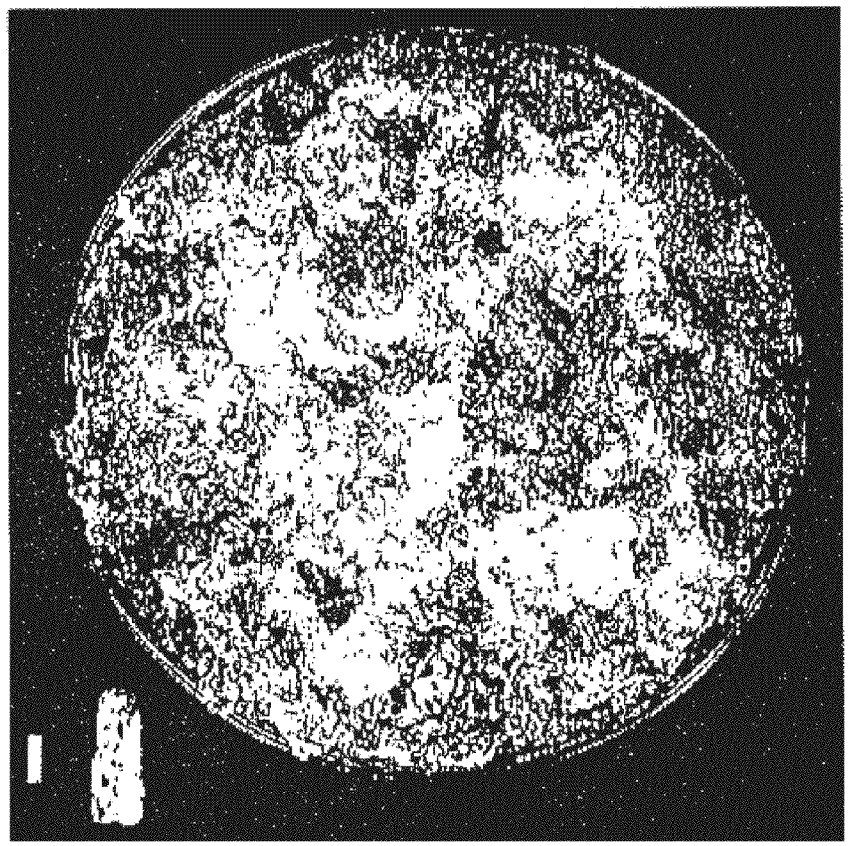
FIG. 8 is a photograph of a gel as formed by cutting off a portion of the hydropolymer resultant from Example 7 and then swelling it with tap water.

In addition, a side view photograph of the hydropolymer as obtained in Example 7 is shown in FIG. 7. In addition, a photograph of a gel as formed by cutting off a portion of the hydropolymer resultant from Example 7 and then swelling it with tap water is shown in FIG. 8. In this photograph of FIG. 8, the hydropolymer outside the Petri dish is the same cut section as that of the hydropolymer which has not yet been swollen with tap water. The longitudinal bars at the lower left of these photographs of FIGS. 7 and 8 are 1 cm long.

TABLE 2

|  | Example 7 | Example 8 | Example 9 | Example 10 | Comparative Example 2 |
|---|---|---|---|---|---|
| Concentration (weight %) in aqueous monomer solution | 55 | 55 | 55 | 55 | 70 |
| Neutralization ratio (mol %) of monomers | 60 | 60 | 60 | 60 | 75 |
| Polymerization initiation temperature (° C.) | 88 | 73 | 60 | 44 | 56 |
| Polymerization peak temperature (° C.) | 111 | 139 | 137 | 121 | 145 |

TABLE 2-continued

|  | Example 7 | Example 8 | Example 9 | Example 10 | Comparative Example 2 |
|---|---|---|---|---|---|
| ΔT (° C.) | 23 | 66 | 73 | 75 | 89 |
| Polymerization time (seconds) | 45 | 60 | 86 | 110 | 35 |
| Solid component concentration (weight %) in hydropolymer | 71 | 68 | 66 | 64 | 89 |
| Concentration ratio | 1.29 | 1.24 | 1.20 | 1.16 | 1.27 |
| GV (g/g) of base polymer | 51 | 48 | 45 | 47 | 23 |
| Extractable content (weight %) of base polymer | 25 | 30 | 28 | 29 | 50 |
| GEX value of base polymer | 11.2 | 9.7 | 9.0 | 9.5 | 2.0 |
| Neutralization ratio (mol %) of base polymer | 65 | 65 | 65 | 64 | 77 |
| Increase (points) of neutralization ratio | 5 | 5 | 5 | 4 | 2 |
| Residual monomer content (ppm) | 300 | 2,000 | 1,600 | 500 | 5,900 |

In addition, a graph which illustrates relations between polymerization reaction temperature and time for the base polymers of Examples 3 and 7 to 10 is shown in FIG. 1.

In Examples 7 to 10, the polymerization initiation temperature was simply changed to 88° C., 73° C., 60° C., and 44° C. under conditions where the composition of the monomers was the same. As the initiation temperature gets higher, the performance of the base polymer gets better, and the solid component concentration of the hydropolymer also becomes higher. In addition, the peak temperature gets lower as the initiation temperature gets higher. The reason for such phenomena is not clear, but the present inventors' inference is as follows.

In the case where the polymerization initiation temperature is low, a hard hydropolymer is formed no later than the attainment to boiling after the initiation, so the boiling temperature becomes high, in other words, the peak temperature also becomes high, and a large plosive is made. In the case where the polymerization initiation temperature is high, no hard hydropolymer is formed no later than the attainment to boiling after the initiation, and an aqueous monomer solution having a high viscosity foams so much with boiling as to enlarge in surface area to emit water vapor well, and the peak temperature is depressed, and the solid component concentration also becomes higher. In addition, almost no plosive is made.

COMPARATIVE EXAMPLE 2

A potassium acrylate solution having a mixed monomer concentration of 70 weight % (neutralization ratio=75 mol %) was prepared by adding 72.1 g of acrylic acid to 22.2 g of ion-exchanged water, and then adding thereto 49.5 g of potassium hydroxide of the purity of 85% as a neutralizing agent and 0.01 g of N,N'-methylenebisacrylamide as a divinyl compound in order.

The aqueous solution as prepared in the above way was kept at 70° C. and then mixed with 2.9 g of a 18 weight % aqueous ammonium persulfate solution (0.5 weight % of the total weight of potassium acrylate, free acrylic acid, and N,N'-methylenebisacrylamide (total weight of the monomer components)) and 1.7 g of a 30.6 weight % aqueous sodium hydrogensulfite solution (0.5 weight %). The resultant mixture solution was placed into a stainless beaker (capacity=2 liters, φ=135 mm) and, as a result, became a layer of about 10 mm in thickness. Then, about 7 seconds later, a polymerization reaction was initiated and then completed in about 1 minute, while the highest temperature was 145° C.

The resultant hydropolymer was solid and easy to pulverize. Thus, a comparative base polymer (2) was obtained, which had a solid component concentration of 89 weight %, a GV of 23 g/g, an extractable content of 50 weight %, a neutralization ratio of 77 mol %, and a residual monomer content of 5,900 ppm.

The results are compiled in Table 2.

This Comparative Example is a trace of Example 1 as set forth in JP-A-071907/1983 (Arakawa Kagaku). It has been found that if the solid component concentration increases to 89 weight %, the extractable content increases greatly.

EXAMPLE 11

A solution (A) was prepared by mixing together 139.5 g of acrylic acid, 0.09 g of polyethylene glycol diacrylate (number-average molecular weight=478), and 0.02 g of 2-hydroxy-2-methyl-1-phenyl-propan-1-one. In addition, an aqueous NaOH solution (B) was prepared by diluting 95.8 g of a 48.5 weight % aqueous NaOH solution with 64.1 g of ion-exchanged water and then adding 0.02 g of diethylenetriaminepentaacetic acid pentasodium salt to the resultant dilution. These solutions were deaerated under a nitrogen atmosphere for 30 minutes. Then, while stirring was carried out with a magnetic stirrer, the solution (A) was added to the solution (B) in an open system all at once to mix them together. A deposit was seen in the initial stage of the mixing step, but instantly dissolved to give an aqueous monomer solution (monomer concentration=55 weight % and neutralization ratio=60 mol %) of which the liquid temperature had risen to about 85° C. due to a heat of neutralization and a heat of dissolution. Furthermore, 0.58 g of a 10 weight % aqueous sodium persulfate solution was added to this aqueous monomer solution, and then the resultant mixture was stirred for several seconds and then immediately poured into a stainless vat type container having a bottom of 200×260 mm (surface temperature=about 64° C.) in an open system (thickness of poured solution=about 5 mm), wherein the container was put on a hot plate of 90° C. and a silicone sheet was attached to the inner surface of the container. The stainless vat type container had the measurements of bottom=200×260 mm, top=560× 460 mm, height=140 mm, and was trapezoidal at the central section, and was open at the top. Immediately thereafter, UV irradiation was carried out with a black light mercury lamp (peak wavelength=352 nm, model No. H400BL, produced by Toshiba Lightech Co., Ltd.) to initiate polymerization. While the polymerization system was emitting water vapor and expanding in all directions and foaming, the polymerization proceeded, and then the polymerization system shrank to almost the same size as the original. The resultant hydropolymer expanded to about 30 times at the maximum of the volume of the aqueous monomer solution according to the eye measurement and then shrank. When the hydropolymer expands, thin portions of the hydropolymer creep up tilt portions of the sides of the container and then, when the hydropolymer shrinks, the thin portions of the hydropolymer return toward their original places, but stop their movements as they are larger than the size of the bottom of the container. This expansion and shrinkage ended within about 1 minute and, when the UV irradiation for 2 minutes had been completed, the hydropolymer was got out. Incidentally, from a temperature measurement chart, it was read that the polymerization initiation temperature was 82° C. and that the highest temperature was 113° C. The resultant hydropolymer (11) was in a much wrinkly form and had a solid component concentration of 70 weight %. Accordingly, the concentration ratio was 1.27. This hydropolymer (11) was pulverized with VERTICAL PULVERIZER (model No. VM27-S, screen mesh opening diameter=3 mm, produced by Orient Co., Ltd.), thus obtaining a flowable particulate hydropolymer (11).

The particulate hydropolymer (11) had a weight-average particle diameter of 1 mm, a GV of 33 g/g, an extractable content of 6 weight %, a residual monomer content of 600 ppm, and a solid component concentration of 71 weight %.

Subsequently, the particulate hydropolymer (11) was dried with hot air in a drying oven of 170° C. for 20 minutes and then pulverized with a roll mill. Next, the pulverized product was classified with screen meshes of the mesh opening sizes of 850 μm and 150 μm, thus obtaining a base polymer (11), most of which had particle diameters of 150 to 850 μm, and which had a weight-average particle diameter of 360 μm.

The base polymer (11) had a GV of 48 g/g, an extractable content of 24 weight %, a neutralization ratio of 65 mol %, and a residual monomer content of 200 ppm. In addition, from observation of particles of the base polymer (11) with a microscope, it was found that: foaming occurred to the polymerization, but most of particles were in a noncrystalline form which contained no bubble nevertheless. The reason therefor seems to be that their bubble sizes were relatively large.

Next, 100 parts of the base polymer (11) was mixed with a surface-crosslinking agent composition solution comprising 0.03 part of ethylene glycol diglycidyl ether, 1 part of propylene glycol, and 5 parts of water, and then the resultant mixture was heated in a drying oven of 80° C. in a sealed container for 1 hour, thus obtaining a surface-crosslinked water-absorbent resin (11) of which the surface vicinity had been crosslinked.

The surface-crosslinked water-absorbent resin (11) had a GV of 34 g/g and an AAP of 32 g/g.

Furthermore, 100 parts of the base polymer (11) was mixed with a surface-crosslinking agent composition solution comprising 0.03 part of ethylene glycol diglycidyl ether, 1 part of propylene glycol, 3 parts of water, and 0.9 part of isopropyl alcohol, and then the resultant mixture was heated in a container as heated with an oil bath of 170° C. for 20 minutes, thus obtaining a surface-crosslinked water-absorbent resin (11a) of which the surface vicinity had been crosslinked.

The surface-crosslinked water-absorbent resin (11a) had a GV of 34 g/g and an AAP of 35 g/g.

EXAMPLE 12

A solution (A) was prepared by mixing together 308.2 g of acrylic acid, 0.20 g of polyethylene glycol diacrylate (number-average molecular weight=478), and 0.04 g of 2-hydroxy-2-methyl-1-phenyl-propan-1-one. In addition, an aqueous NaOH solution (B) was prepared by diluting 194.1 g of a 48.5 weight % aqueous NaOH solution with 97.0 g of ion-exchanged water. Then, while stirring was carried out with a magnetic stirrer, the solution (A) was added to the solution (B) in an open system all at once to mix them together. A deposit was seen in the initial stage of the mixing step, but instantly dissolved to give an aqueous monomer solution (monomer concentration=60 weight %, neutralization ratio=55 mol %, temperature=102° C.) (this aqueous monomer solution preparation operation was carried out in another batch in the same way, and the amount of dissolved oxygen was measured, so that it was 0.7 ppm). Furthermore, 1.3 g of a 10 weight % aqueous sodium persulfate solution was added to this aqueous monomer solution, and then the resultant mixture was stirred for several seconds and then immediately poured into a stainless vat type container in an open system, wherein the container was put on a hot plate of 90° C. and a silicone sheet was attached to the inner surface of the container. The stainless vat type container had the measurements of bottom=200×260 mm, top=560×460 mm, height=140 mm, and was trapezoidal at the central section, and was open at the top. Immediately thereafter, UV irradiation was carried out with a black light mercury lamp (peak wavelength=352 nm, model No. H400BL, produced by Toshiba Lightech Co., Ltd.) to initiate polymerization. While the polymerization system was emitting water vapor and expanding in all directions and foaming, the polymerization proceeded (expansion magnification=40 times). When the UV irradiation for 2 minutes had been completed, the resultant hydropolymer was got out. This hydropolymer had a solid component concentration of 77 weight %. This hydropolymer was pulverized with a screen of 1 mm in mesh opening diameter in VERTICAL PULVERIZER (model No. VA/127-S, screen mesh opening diameter=3 mm, produced by Orient Co., Ltd.), thus obtaining a flowable particulate hydropolymer. Then, this particulate hydropolymer was classified with screen meshes of the mesh opening sizes of 850 μm and 150 μm, thus obtaining a particulate hydropolymer (12) having a weight-average particle diameter of 500 μm.

The particulate hydropolymer (12) has a GV of 22 g/g, an extractable content of 2 weight %, a residual monomer content of 600 ppm, and a solid component concentration of 79 weight %.

EXAMPLE 13

A solution (A) was prepared by mixing together 279.0 g of acrylic acid, 0.09 g of polyethylene glycol diacrylate (number-average molecular weight=478), and 0.03 g of 2-hydroxy-2-methyl-1-phenyl-propan-1-one. In addition, an aqueous NaOH solution (B) was prepared by diluting 191.54 g of a 48.5 weight % aqueous NaOH solution with 128.2 g of ion-exchanged water. Then, while stirring was carried out with a magnetic stirrer, the solution (A) was added to the solution (B) in an open system all at once to mix them together. A deposit was seen in the initial stage of the mixing step, but instantly dissolved to give an aqueous monomer solution (monomer concentration=55 weight %, neutralization ratio=60 mol %, temperature=92° C.) (this aqueous monomer solution preparation operation was carried out in another batch in the same way, and the amount of dissolved oxygen was measured, so that it was 1.4 ppm). Furthermore, 1.3 g of a 10 weight % aqueous sodium persulfate solution was added to this aqueous monomer solution, and then the resultant mixture was stirred for several seconds and then immediately poured into a stainless vat type container in an open system, wherein the container was put on a hot plate of 90° C. and a silicone sheet was attached to the inner surface of the container. The stainless vat type container had the measurements of bottom=200×260 mm, top=560×460 mm, height=140 mm, and was trapezoidal at the central section, and was open at the top. Immediately thereafter, UV irradiation was carried out with a black light mercury lamp (peak wavelength=352 nm, model No. H400BL, produced by Toshiba Lightech Co., Ltd.) to initiate polymerization. While the polymerization system was emitting water vapor and expanding in all directions and foaming, the polymerization proceeded (expansion magnification=35 times). When the UV irradiation for 2 minutes had been completed, the resultant hydropolymer was got out (solid component concentration=69 weight %). This hydropolymer was pulverized with VERTICAL PULVERIZER (model No. VM27-S, produced by Orient Co., Ltd.) wherein the hydropolymer was first pulverized with a screen of 3 mm in mesh opening diameter and then further Pulverized with a screen of 1 mm in mesh opening diameter, thus obtaining a flowable particulate hydropolymer. Then, this particulate hydropolymer was classified with screen meshes of the mesh opening sizes of 850 μm and 150 μm, thus obtaining a particulate hydropolymer (13) having a weight-average particle diameter of 610 μm (solid component concentration=70 weight %).

The particulate hydropolymer (13) has a GV of 34 g/g, an extractable content of 10 weight %, and a residual monomer content of 700 ppm.

Next, 100 parts of the particulate hydropolymer (13) was mixed with a surface-crosslinking agent composition solution comprising 0.02 part of ethylene glycol diglycidyl ether and 0.2 part of propylene glycol, and then the resultant mixture was heated in a drying oven of 80° C. in a sealed container for 1 hour. The particles once aggregated together after this heating, but could easily be disintegrated into a particulate form by cooling to room temperature. Thus obtained was a surface-crosslinked water-absorbent resin (13) of which the surface vicinity had been crosslinked.

The surface-crosslinked water-absorbent resin (13) has a GV of 25 g/g, an AAP of 23 g/g, a residual monomer content of 200 ppm, and a solid component concentration of 74 weight %.

EXAMPLE 14

A sheet of the hydropolymer (11) in a much wrinkly form, as obtained in Example 11, was cut into roughly four with a circular saw, and then placed into TURBO CUTTER(C-300, produced by Turbo Kogyo Co., Ltd.) having a screen mesh opening diameter of 3 mm, and then disintegrated, thus obtaining a particulate hydropolymer (14). About 50 kg of the hydropolymer (11) could be treated in 30 minutes.

The resultant particulate hydropolymer (14) had a solid component concentration of 71 weight % and a weight-average particle diameter of 1.3 mm. Its particle diameter distribution as determined with a Ro-Tap type screen shaker was as follows.

| | |
|---|---|
| Particulate hydropolymer having particle diameters of not smaller than 2 mm: | 9 weight % |
| Particulate hydropolymer having particle diameters in the range of 1.4 to 2 mm, but not including 2 mm: | 38 weight % |
| Particulate hydropolymer having particle diameters in the range of 1 to 1.4 mm, but not including 1.4 mm: | 31 weight % |
| Particulate hydropolymer having particle diameters in the range of 0.5 to 1 mm, but not including 1 mm: | 19 weight % |
| Particulate hydropolymer having particle diameters of smaller than 0.5 mm: | 3 weight % |

EXAMPLE 15

The particulate hydropolymer (14), as obtained by disintegration with the TURBO CUTTER in Example 14, was placed into TURBO GRINDER (TG-300, produced by Turbo Kogyo Co., Ltd.) and then further disintegrated, thus obtaining a particulate hydropolymer (15).

Shown in Table 4 are: the screen mesh opening diameter of the TURBO GRINDER; and the weight-average particle diameter and the solid component concentration of the disintegrated particulate hydropolymer (15).

EXAMPLE 16

The particulate hydropolymers (14) and (15) were dried with a fluidized-bed drier (Pulvis GB22, produced by Yamato Kagaku Co., Ltd.) under conditions of internal temperature=180° C., material=100 g, hot-air flow rate=0.35 m³/minute.

Shown in Table 3 are the following measured values: the material temperature during the drying and the solid component concentration after the drying of the particulate hydropolymers (14) and (15); and the GV, the extractable content, and the residual monomer content of the dried particulate hydropolymers (14) and (15) as obtained by pulverizing the dried products and then classifying the pulverized products into the particle diameter range of 300 to 600 μm.

TABLE 3

| | Dried particulate hydropolymer (14) | Dried particulate hydropolymer (15) |
|---|---|---|
| Temperature (° C.) of materials at drying time of 1 minute | 105 | 90 |
| Temperature (° C.) of materials at drying time of 2 minutes | 140 | 127 |
| Temperature (° C.) of materials at drying time of 3 minutes | 159 | 145 |
| Temperature (° C.) of materials at drying time of 5 minutes | 171 | 161 |
| Temperature (° C.) of materials at drying time of 10 minutes | 179 | 173 |

TABLE 3-continued

|  | Dried particulate hydropolymer (14) | Dried particulate hydropolymer (15) |
|---|---|---|
| Solid component concentration (weight %) after drying for 10 minutes | 95 | 96 |
| GV (g/g) | 44 | 42 |
| Extractable content (weight %) | 18 | 16 |
| Residual monomer content (ppm) | 250 | 300 |

EXAMPLE 17

A sheet of the hydropolymer (11) in a much wrinkly form, as obtained in Example 11, was cut into roughly four with a circular saw, and then continuously supplied into ROTOPLEX (28/40Ro, produced by Hosokawa Mikron Co., Ltd.) having a screen mesh opening diameter of 2 mm. The treatment rate was about 70 kg/hour.

The particulate hydropolymer (17), as obtained by collection with a cyclone after the disintegration, had a solid component concentration of 72 weight % and a weight-average particle diameter of about 1 mm. Its particle diameter distribution as determined with a Ro-Tap type screen shaker was as follows.

| Particulate hydropolymer having particle diameters of not smaller than 2 mm: | 1 weight % |
|---|---|
| Particulate hydropolymer having particle diameters in the range of 1.2 to 2 mm, but not including 2 mm: | 29 weight % |
| Particulate hydropolymer having particle diameters in the range of 0.85 to 1.2 mm, but not including 1.2 mm: | 35 weight % |
| Particulate hydropolymer having particle diameters in the range of 0.3 to 0.85 mm, but not including 0.85 mm: | 26 weight % |
| Particulate hydropolymer having particle diameters of smaller than 0.3 mm: | 9 weight % |

EXAMPLE 18

A sheet of the hydropolymer (11) in a much wrinkly form, as obtained in Example 11, was cut into roughly four with a circular saw, and then continuously supplied into ROTOPLEX (28/40Ro, produced by Hosokawa Mikron Co., Ltd.) having a screen mesh opening diameter of 5 mm. The treatment rate was about 100 kg/hour.

The particulate hydropolymer (18), as obtained by collection with a cyclone after the disintegration, had a solid component concentration of 71 weight % and a weight-average particle diameter of 2 mm. Its particle diameter distribution as determined with a Ro-Tap type screen shaker was as follows.

| Particulate hydropolymer having particle diameters of not smaller than 2.8 mm: | 6 weight % |
|---|---|
| Particulate hydropolymer having particle diameters in the range of 1.7 to 2.8 mm, but not including 2.8 mm: | 58 weight % |
| Particulate hydropolymer having particle diameters in the range of 0.85 to 1.7 mm, but not including 1.7 mm: | 29 weight % |
| Particulate hydropolymer having particle diameters in the range of 0.15 to 0.85 mm, but not including 0.85 mm: | 6 weight % |
| Particulate hydropolymer having particle diameters of smaller than 0.15 mm: | 1 weight % |

Next, this disintegrated particulate hydropolymer (18) was placed into DRY MEISTER (apparatus to simultaneously carry out pulverization and drying by hot air and a dispersing rotor, produced by Hosokawa Mikron Co., Ltd.) wherein the hot-air temperature was 270° C. and the dispersing rotor was rotated at 3,000 rpm.

The particle diameter distribution of the particulate hydropolymer (18a) (dried and then collected with a cyclone), as determined with a Ro-Tap type screen shaker, was as follows.

| Particulate hydropolymer having particle diameters of not smaller than 2.8 mm: | 1 weight % |
|---|---|
| Particulate hydropolymer having particle diameters in the range of 1.7 to 2.8 mm, but not including 2.8 mm: | 5 weight % |
| Particulate hydropolymer having particle diameters in the range of 0.85 to 1.7 mm, but not including 1.7 mm: | 24 weight % |
| Particulate hydropolymer having particle diameters in the range of 0.15 to 0.85 mm, but not including 0.85 mm: | 59 weight % |
| Particulate hydropolymer having particle diameters of smaller than 0.15 mm: | 11 weight % |

The particulate hydropolymer (18a) had a solid component concentration of 94 weight % and a weight-average particle diameter of 0.4 mm. No adhered matter was seen inside the DRY MEISTER after its operation.

This dried and pulverized particulate hydropolymer (18a) had a GV of 40 g/g, an extractable content of 15 weight %, and a residual monomer content of 400 ppm.

EXAMPLE 19

A sheet of the hydropolymer (11) in a much wrinkly form, as obtained in Example 11, was cut into roughly four with a circular saw, and then placed into a laboratory pulverizer (FDS-model produced by Miyako Bussan Co., Ltd., screen mesh opening diameter=1 mm, hammer crusher type pulverizer), but the hydropolymer instantly jammed and was therefore not discharged. Thus, a dust collector (Model 406 for both dry and wet business uses, produced by Makita Co., Ltd.) was connected to the discharging outlet in order to make an air stream in the pulverizer. As a result, the hydropolymer became smoothly discharged. The discharged matter had a solid component concentration of 78 weight % and a weight-average particle diameter of 650 μm, and the ratio of its portions having particle diameters of not larger than 150 μm was 7 weight %.

It is considered that the air streaming during the pulverization could reduce the adhesion of the materials by quickly carrying away water as emitted by heat generation during the pulverization, so that it became possible to do the pulverization.

EXAMPLE 20

A sheet of the hydropolymer (11) in a much wrinkly form, as obtained in Example 11, was cut into roughly four with a circular saw, and then placed into CUTTER MILL (UG03-280LFT, screen mesh opening diameter=8 mm, produced by Horai Co., Ltd.). Incidentally, a blower (DF type fan, DF-3, blow speed=15 m³/min, produced by Horai Co., Ltd.) and a cyclone were connected to this CUTTER MILL, and the disintegrated product was obtained from the lower part of the cyclone. The particulate hydropolymer (20) as obtained by the disintegration had a solid component concentration of 72 weight % and a weight-average particle diameter of 3 mm. Its particle diameter distribution as determined with a Ro-Tap type screen shaker was as follows.

| | |
|---|---|
| Particulate hydropolymer having particle diameters of not smaller than 4 mm: | 17 weight % |
| Particulate hydropolymer having particle diameters in the range of 2 to 4 mm, but not including 4 mm: | 69 weight % |
| Particulate hydropolymer having particle diameters in the range of 1 to 2 mm, but not including 2 mm: | 13 weight % |
| Particulate hydropolymer having particle diameters of smaller than 1 mm: | 1 weight % |

Next, this particulate hydropolymer (20) was placed into MESHMILL (HA8-2542, screen mesh opening diameter=2 mm, produced by Horai Co., Ltd.) and then further disintegrated. The particulate hydropolymer (20a) as collected with a cyclone had a solid component concentration of 75 weight % and a weight-average particle diameter of 0.6 mm. The treatment rate was 130 kg/hour. The particle diameter distribution of this particulate hydropolymer (20a), as determined with a Ro-Tap type screen shaker, was as follows.

| | |
|---|---|
| Particulate hydropolymer having particle diameters of not smaller than 1.4 mm: | 0 weight % |
| Particulate hydropolymer having particle diameters in the range of 1 to 1.4 mm, but not including 1.4 mm: | 8 weight % |
| Particulate hydropolymer having particle diameters in the range of 0.85 to 1 mm, but not including 1 mm: | 17 weight % |
| Particulate hydropolymer having particle diameters in the range of 0.15 to 0.85 mm, but not including 0.85 mm: | 72 weight % |
| Particulate hydropolymer having particle diameters of smaller than 0.15 mm: | 3 weight % |

No adhered matter was seen inside the MESHMILL after its operation.

EXAMPLE 21

An aqueous monomer solution having a monomer concentration of 50 weight %, a neutralization ratio of 65 mol %, and a temperature of 86° C. was prepared by mixing together 83.5 parts of acrylic acid, 62.1 parts of a 48.5 weight % aqueous NaOH solution, 54.3 parts of ion-exchanged water, 0.11 part of polyethylene glycol diacrylate (number-average degree of polymerization of ethylene oxide=8) as a crosslinking agent, and 0.01 part of 2-hydroxy-2-methyl-1-phenyl-propan-1-one as an initiator (this aqueous monomer solution preparation operation was carried out in another batch in the same way, and the amount of dissolved oxygen was measured, so that it was 3.0 ppm). This aqueous monomer solution was poured into a Teflon-coated stainless container having a bottom of 200×260 mm, wherein the container was put on a hot plate of 90° C. and nitrogen gas was being introduced into the container. When the temperature of the aqueous monomer solution became 80° C., this solution was irradiated with ultraviolet rays by a black light fluorescent lamp for 10 minutes (quantity of light=780 mJ/cm$^2$), thus obtaining a hydropolymer (21) of about 3 mm in thickness. This hydropolymer had a solid component concentration of 60 weight %. Accordingly, the concentration ratio was 1.20. The highest temperature was 110° C. during the polymerization. The hydropolymer (21) was cut into fine pieces with VERTICAL PULVERIZER (model No. VM27-S, screen mesh opening diameter=3 mm, produced by Orient Co., Ltd.), thus obtaining a particulate hydropolymer (21) having a weight-average particle diameter of 1.6 mm and a solid component concentration of 61 weight %. This particulate hydropolymer (21) was dried with hot air of 170° C. for 30 minutes and then pulverized with a laboratory pulverizer. Next, the pulverized product was classified with screen meshes of the mesh opening sizes of 600 μm and 300 μm, thus obtaining a base polymer (21), most of which had particle diameters of 300 to 600 μm.

The base polymer (21) had a GV of 58 g/g, an extractable content of 16 weight %, a neutralization ratio of 68 mol %, and a residual monomer content of 2,200 ppm.

Next, 100 parts of the base polymer (21) was mixed with a surface-crosslinking agent composition solution comprising 0.05 part of ethylene glycol diglycidyl ether, 1 part of propylene glycol, and 2 parts of water, and then the resultant mixture was heated in a drying oven of 80° C. for 40 minutes, thus obtaining a surface-crosslinked water-absorbent resin (21) of which the surface vicinity had been crosslinked.

The surface-crosslinked water-absorbent resin (21) had a GV of 42 g/g and an AAP of 36 g/g.

Table 4 is a compilation about the disintegration of the hydropolymers of Examples 11 to 15 and 17 to 21.

TABLE 4

| | Solid component concentration (weight %) in hydropolymer | Disintegrating machine name | Screen mesh opening diameter (mm) of disintegrating machine | Solid component concentration (weight %) in particulate hydropolymer | Weight-average particle diameter (mm) of particulate hydropolymer |
|---|---|---|---|---|---|
| Example 11 | 70 | VERTICAL PULVERIZER | 3 | 71 | 1 |
| Example 12 | 77 | VERTICAL PULVERIZER | 1 | 79 | 0.5 |
| Example 13 | 69 | VERTICAL PULVERIZER | 3.1 | 70 | 0.61 |
| Example 14 | 70 | TURBO CUTTER | 3 | 71 | 1.3 |
| Example 15 | 71 | TURBO GRINDER | 1 | 72 | 0.82 |
| Example 15 | 71 | TURBO GRINDER | 0.7 | 73 | 0.58 |
| Example 17 | 70 | ROTOPLEX | 2 | 72 | 1 |
| Example 18 | 70 | ROTOPLEX | 5 | 71 | 2 |
| Example 18 | 71 | DRY MEISTER | — | 94 | 0.4 |
| Example 19 | 70 | FDS | 1 | 78 | 0.65 |
| Example 20 | 70 | CUTTER MILL | 8 | 72 | 3 |
| Example 20 | 72 | MESHMILL | 2 | 75 | 0.6 |
| Example 21 | 60 | VERTICAL PULVERIZER | 3 | 61 | 1.6 |

COMPARATIVE EXAMPLE 3

A sheet of the hydropolymer (11) in a much wrinkly form, as obtained in Example 11, was cut into roughly four with a circular saw and then placed into a meat chopper having dies of the aperture of 8 mm (produced by Hiraga Seisakusho Co., Ltd.). As a result, the burden was so heavy as to immediately stop the operation, therefore the disintegration could not be carried out.

COMPARATIVE EXAMPLE 4

A sheet of the hydropolymer (11) in a much wrinkly form, as obtained in Example 11, was cut into roughly four with a circular saw and then placed into a sample mill (KIIW-1 model, produced by Fuji Paudal Industry Co., Ltd.) having a screen mesh opening diameter of 3 mm. As a result, the burden was so heavy as to immediately stop the operation, therefore the disintegration could not be carried out.

COMPARATIVE EXAMPLE 5

A sheet of the hydropolymer (11) in a much wrinkly form, as obtained in Example 11, was then placed into a kneader (capacity=2.5 liters, produced by Koike Tekko Co., Ltd.) having sigma type blades. As a result, the hydropolymer was kneaded, but could not be disintegrated.

COMPARATIVE EXAMPLE 6

A sheet of the hydropolymer (11) in a much wrinkly form, as obtained in Example 11, was cut into roughly four with a circular saw and then placed into an apparatus of FIG. 4 as drawn in JP-A-188727/1999. As a result, the hydropolymer twined around the shaft, and therefore could not be disintegrated.

COMPARATIVE EXAMPLE 7

A reaction solution was prepared by dissolving 9.25 g of polyethylene glycol diacrylate (number-average degree of polymerization of ethylene oxide=8) into 5,500 g of an aqueous solution of sodium acrylate having a neutralization ratio of 55 mol % (monomer concentration=30 weight %). Next, this solution was deaerated under a nitrogen gas atmosphere for 30 minutes, and then the resultant solution was supplied into a reactor as prepared by lidding a jacketed stainless-steel-made twin-arm kneader of 10 liters in capacity having two sigma type blades. While maintaining the reaction solution at 30° C., the internal air of the system was replaced with nitrogen gas. Next, while the reaction solution was stirred, 1.91 g of 2,2'-azobis(2-amidinopropane) dihydrochloride, 0.96 g of sodium persulfate and 0.10 g of L-ascorbic acid were added, with the result that a polymerization reaction started about 1 minute after. Then, this polymerization reaction was carried out in the range of 30 to 80° C. and, 60 minutes after the initiation of the polymerization reaction, the resultant hydropolymer was got out. The resultant hydropolymer had a finely divided diameter of about 5 mm. This finely divided hydropolymer was spread onto a 50-mesh metal gauze and then dried at 150° C. with hot air for 90 minutes. Then, the resultant dried product was pulverized with a vibration mill and then classified with a 20-mesh metal gauze, thus obtaining a comparative base polymer (7) of the irregular pulverized shape having a weight-average particle diameter of 300 μm. Next, 100 parts of the resultant comparative base polymer (7) was mixed with a surface-crosslinking agent composition solution comprising 0.005 part of diethylenetriaminepentaacetic acid pentasodium salt, 1 part of propylene glycol, 0.05 part of ethylene glycol diglycidyl ether, 3 parts of water, and 1 part of isopropyl alcohol. The resultant mixture was heated at 210° C. for 45 minutes, thus obtaining a comparative surface-crosslinked water-absorbent resin (7).

COMPARATIVE EXAMPLE 8

An aqueous monomer solution was prepared by mixing 67.0 parts of a 37 weight % aqueous sodium acrylate solution, 10.2 parts of acrylic acid, 0.155 part of polyethylene glycol diacrylate (number-average degree of polymerization of ethylene oxide=8), and 22.0 parts of water together. Nitrogen was blown into the above aqueous monomer solution in a vat, thus reducing the concentration of dissolved oxygen in the aqueous monomer solution to not higher than 0.1 ppm. Then, the temperature of the above aqueous monomer solution was adjusted to 18° C. under nitrogen atmosphere. Next, thereto 0.16 part of a 5 weight % aqueous sodium persulfate solution, 0.16 part of a 5 weight % aqueous 2,2' azobis(2-amidinopropane) dihydrochloride solution, 0.15 part of a 0.5 weight % aqueous L-ascorbic acid solution, and 0.17 part of a 0.35 weight % aqueous hydrogen peroxide solution were dropwise added in sequence under stirred conditions. After the dropwise addition of hydrogen peroxide, a polymerization reaction immediately started and, 10 minutes later, the temperature of the aqueous monomer solution reached the peak temperature of 85° C. Then, the vat was immersed into a hot water bath of 80° C. and aged for 15 minutes. The resultant transparent hydropolymer was crushed with a meat chopper. The resultant finely divided hydropolymer was spread onto a 50-mesh metal gauze and then dried at 160° C. with hot air for 65 minutes. Then, the resultant dried product was pulverized with a pulverizing machine and then classified into what passed through a screen of 850 μm but remained on a screen of 106 μm, thus obtaining a comparative base polymer (8) of the irregular pulverized shape having a weight-average particle diameter of 320 μm. Next, 100 parts of the resultant comparative base polymer (8) was mixed with a surface-crosslinking agent composition solution comprising 1 part of propylene glycol, 0.5 part of 1,4-butanediol, 3 parts of water, and 1 part of isopropyl alcohol. The resultant mixture was heated at 210° C. for 40 minutes, thus obtaining a comparative surface-crosslinked water-absorbent resin (8).

In addition, shown in Table 5 are the results of comparison of GV, AAP, solubilization residue ratio, GV×solubilization residue ratio among the surface-crosslinked water-absorbent resins (2), (3), (5), (6) of Examples 2, 3, 5, 6, comparative surface-crosslinked water-absorbent resins (1), (7), (8) of Comparative Examples 1, 7, 8, comparative base polymers (1), (7), (8) of Comparative Examples 1, 7, 8, and water-absorbent resins which are products of other makers.

TABLE 5

| | Synthetic example or maker name | GV (g/g) | AAP (g/g) | Solubilization residue ratio (%) | GV × solubilization residue ratio ((g/g)%) |
|---|---|---|---|---|---|
| Surface-crosslinked water-absorbent resin (2) | Example 2 | 42 | 36 | 25 | 1,050 |
| Surface-crosslinked water-absorbent resin (3) | Example 3 | 34 | 36 | 21 | 714 |
| Surface-crosslinked water-absorbent resin (5) | Example 5 | 25 | 26 | 18 | 450 |
| Surface-crosslinked water-absorbent resin (6) | Example 6 | 23 | 24 | 25 | 575 |
| Comparative surface-crosslinked water-absorbent resin (1) | Comparative Example 1 | 28 | 26 | 73 | 2,044 |
| Comparative base polymer (7) | Comparative Example 7 | 48 | — | 41 | 1,968 |
| Comparative surface-crosslinked water-absorbent resin (7) | Comparative Example 7 | 33 | 30 | 49 | 1,617 |
| Comparative base polymer (8) | Comparative Example 8 | 39 | — | 60 | 2,340 |
| Comparative surface-crosslinked water-absorbent resin (8) | Comparative Example 8 | 28 | 28 | 65 | 1,820 |
| SXM-75 | Stockhausen | 32 | 29 | 43 | 1,376 |
| SXM-77 | Stockhausen | 31 | 25 | 62 | 1,922 |
| ASAP2300 | BASF | 31 | 26 | 68 | 2,108 |
| ASAP2300 | BASF | 24 | 24 | 84 | 2,016 |
| Drytech | Dow | 30 | 31 | 60 | 1,800 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbent resin, which is obtained by a process including the step of polymerizing an aqueous solution of water-absorbent resin-forming monomers including acrylic acid and/or its salt as major components, and has the following properties:
   (1) 20 (g/g)≦absorption capacity without load (GV)≦60 (g/g);
   (2) absorption capacity under a load (AAP)≧20 (g/g); and
   (3) absorption capacity without load (GV)×solubilization residue ratio (%)≦1,200 ((g/g)%).

2. A water-absorbent resin according to claim 1, which is obtained by a process including the step of polymerizing an aqueous solution of water-absorbent resin-forming monomers including acrylic acid and/or its salt as major components, wherein:
   (1) the aqueous solution has a monomer component concentration of not less than 50 weight %; and
   (2) an internal-crosslinking agent is used in a ratio of not larger than 0.02 mol % to the entirety of the water-absorbent resin-forming monomers;
   and wherein the process further includes the steps of:
   (3) surface-crosslinking the water-absorbent resin; and
   (4) adding a chelating agent to the water-absorbent resin in a ratio of not less than 10 ppm thereto.

3. A disintegrated hydropolymer, which is obtained when producing a water-absorbent resin by a process including the step of polymerizing an aqueous solution of water-absorbent resin-forming monomers including acrylic acid and/or its salt as major components, and has a solid component concentration in the range of 55 to 82 weight %, a residual monomer content of not more than 1,000 ppm, and a weight-average particle diameter of not larger than 3 mm.

4. A hydropolymer according to claim 3, which is a surface-crosslinked one.

5. A sanitary article, which comprises the water-absorbent resin as recited in claim 1.

6. A sanitary article according to claim 5, which is a disposable diaper.

* * * * *